US010610099B2

(12) United States Patent
Artemiadis et al.

(10) Patent No.: US 10,610,099 B2
(45) Date of Patent: Apr. 7, 2020

(54) SYSTEMS AND METHODS FOR SIMULTANEOUS POSITION AND IMPEDANCE CONTROL FOR MYOELECTRIC INTERFACES

(71) Applicant: ARIZONA BOARD OF REGENTS ON BEHALF OF ARIZONA STATE UNIVERSITY, Tempe, AZ (US)

(72) Inventors: Panagiotis Artemiadis, Phoenix, AZ (US); Mark Ison, San Jose, CA (US)

(73) Assignee: Arizona Board of Regents on Behalf of Arizona State University, Tempe, AZ (US)

( * ) Notice: Subject to any disclaimer, the term of this patent is extended or adjusted under 35 U.S.C. 154(b) by 202 days.

(21) Appl. No.: 15/611,998

(22) Filed: Jun. 2, 2017

(65) Prior Publication Data
US 2017/0348851 A1 Dec. 7, 2017

Related U.S. Application Data

(60) Provisional application No. 62/346,644, filed on Jun. 7, 2016.

(51) Int. Cl.
*B25J 9/00* (2006.01)
*A61B 5/0488* (2006.01)
(Continued)

(52) U.S. Cl.
CPC ........ *A61B 5/0004* (2013.01); *A61B 5/04888* (2013.01); *B25J 13/087* (2013.01)

(58) Field of Classification Search
CPC .............. A61B 5/0004; A61B 5/04888; A61B 5/0488–0492; A61B 5/4851;
(Continued)

(56) References Cited

U.S. PATENT DOCUMENTS 9,707,442 B2 7/2017 Artemiadis et al.
9,757,610 B2 9/2017 Artemiadis et al.
(Continued)

FOREIGN PATENT DOCUMENTS

WO 2014070672 A1 5/2014
WO 2015065948 A1 5/2015
(Continued)

OTHER PUBLICATIONS

Sartori, M. et al., "A lower limb EMG-driven biomechanical model for applications in rehabilitation robotics", 2009 International Conference on Advanced Robotics (Munich, Germany, Jun. 22-26, 2009), 2009 (date added to IEEE Xplore: Jul. 2009), 7 pages.
(Continued)

*Primary Examiner* — Adam R Mott
(74) *Attorney, Agent, or Firm* — Polsinelli PC

(57) ABSTRACT

Systems and methods for simultaneous position and impedance control for myoelectric interfaces are disclosed herein. Properties such as control refinement, retention, generalization, and transfer allow users to learn simultaneous and proportional motion simply by interacting with a myoelectric interface, regardless of its initial intuitiveness. The presently disclosed technology expands on these motor learning approaches by implementing a multidirectional impedance controller in this framework. Using sEMG inputs from upper limb muscles, users simultaneously control both the stiffness and set-point of 3-DOFs. Users stabilize control in the presence of external forces in an analogous way to natural limb movements. Despite having no haptic feedback, subjects learn to tune the stiffness of the object being controlled to stabilize movement along desired paths.

20 Claims, 13 Drawing Sheets
(12 of 13 Drawing Sheet(s) Filed in Color)

(51) Int. Cl.
A61B 5/00 (2006.01)
B25J 13/08 (2006.01)

(58) Field of Classification Search
CPC ... A61B 5/04001; B25J 13/087; B25J 9/0006; A61H 2230/60; A61H 2230/605; A61F 2002/482; A61F 2002/704; A61F 2/72; A61F 2/68; A61M 2230/005; A61M 2230/10; G06F 3/015; A61N 1/0551
See application file for complete search history.

(56) References Cited

U.S. PATENT DOCUMENTS

| | | | |
|---|---|---|---|
| 9,833,895 B2 | 12/2017 | Artemiadis et al. | |
| 10,285,828 B2* | 5/2019 | Herr | A61F 2/60 |
| 2012/0004736 A1* | 1/2012 | Goldfarb | A61F 2/60 623/25 |
| 2012/0188158 A1* | 7/2012 | Tan | A61B 5/0488 345/156 |
| 2017/0061828 A1 | 3/2017 | Artemiadis et al. | |
| 2018/0164835 A1 | 6/2018 | Artemiadis et al. | |
| 2019/0160653 A1 | 5/2019 | Artemiadis et al. | |
| 2019/0217465 A1 | 7/2019 | Artemiadis et al. | |

FOREIGN PATENT DOCUMENTS

| | | |
|---|---|---|
| WO | 2018022689 A1 | 2/2018 |
| WO | 2018022692 A1 | 2/2018 |
| WO | 2018081569 A1 | 5/2018 |

OTHER PUBLICATIONS

Scheme, E. et al., "Electromyogram pattern recognition for control of powered upper-limb prostheses: State of the art and challenges for clinical use", Journal of Rehabilitation Research & Development, 2011, vol. 48, No. 6, pp. 643-660 <DOI:10.1682/JRRD.2010.09.0177>.

Scheme, E. et al., "Examining the adverse effects of limb position on pattern recognition based myoelectric control", Annual International Conference of the IEEE Engineering in Medicine and Biology (Buenos Aires, Argentina, Aug. 31-Sep. 4, 2010), 2010 (date added to IEEE Xplore: Nov. 2011), pp. 6337-6340 <DOI:10.1109/IEMBS.2010.5627638>.

Scheme, E. et al., "Motion Normalized Proportional Control for Improved Pattern Recognition-Based Myoelectric Control", IEEE Transactions on Neural Systems and Rehabilitation Engineering, Jan. 2014 (date of publication: Mar. 2013), vol. 22, No. 1, pp. 149-157 <DOI:10.1109/TNSRE.2013.2247421>.

Scheme, E. et al., "Selective Classification for Improved Robustness of Myoelectric Control Under Nonideal Conditions", IEEE Transactions on Biomedical Engineering, Jun. 2011 (date of publication: Feb. 2011), vol. 58, No. 6, pp. 1698-1705 <DOI:10.1109/TBME.2011.2113182>.

Scheme, E. et al., "Validation of a Selective Ensemble-Based Classification Scheme for Myoelectric Control Using a Three-Dimensional Fitts' Law Test", IEEE Transactions on Neural Systems and Rehabilitation Engineering, Jul. 2013 (date of publication: Oct. 2012), vol. 21, No. 4, pp. 616-623 <DOI:10.1109/TNSRE.2012.2226189>.

Schultz, A. et al., "Neural Interfaces for Control of Upper Limb Prostheses: The State of the Art and Future Possibilities", PM&R, Jan. 2011, vol. 3, No. 1, pp. 55-67 <DOI:10.1016/j.pmrj.2010.06.016>.

Scott, R., "Myoelectric Control of Prostheses and Orthoses", Bulletin of Prosthetics Research, Spring 1967, pp. 93-114.

Sears, H. et al., "Proportional myoelectric hand control: an evaluation", American Journal of Physical Medicine & Rehabilitation, Feb. 1991, vol. 70, No. 1, pp. 20-28.

Seidler, R., "Neural Correlates of Motor Learning, Transfer of Learning, and Learning to Learn", Exercise and Sport Science Reviews, Jan. 2010, vol. 38, No. 1, pp. 3-9 <DOI:10.1097/JES.0b013e3181c5cce7>.

Sensinger, J. et al., "Adaptive Pattern Recognition of Myoelectric Signals: Exploration of Conceptual Framework and Practical Algorithms", IEEE Transactions on Neural Systems and Rehabilitation Engineering, Jun. 2009, vol. 17, No. 3, pp. 270-278 <DOI:10.1109/TNSRE.2009.2023282>.

Shenoy, P. et al., "Online Electromyographic Control of a Robotic Prosthesis", IEEE Transactions on Biomedical Engineering, Mar. 2008 (date of publication: Feb. 2008), vol. 55, No. 3, pp. 1128-1135 <DOI:10.1109/TBME.2007.909536>.

Simon, A. et al., "A comparison of proportional control methods for pattern recognition control", Annual International Conference of the IEEE Engineering in Medicine and Biology Society (Boston, MA, Aug. 30-Sep. 3, 2011), 2011 (date added to IEEE Xplore: Dec. 2011), pp. 3354-3357 <DOI:10.1109/IEMBS.2011.6090909>.

Simon, A. et al., "A Decision-Based Velocity Ramp for Minimizing the Effect of Misclassifications During Real-Time Pattern Recognition Control", IEEE Transactions on Biomedical Engineering, Aug. 2011 (date of publication: May 2011), vol. 58, No. 8, pp. 2360-2368 <DOI:10.1109/TBME.2011.2155063>.

Simon, A. et al., "Patient Training for Functional Use of Pattern Recognition-Controlled Prostheses", Journal of Prosthetics and Orthotics, Apr. 2012, vol. 24, No. 2, pp. 56-64 <DOI:10.1097/JPO.0b013e3182515437>.

Simon, A. et al., "Target Achievement Control Test: evaluating real-time myoelectric pattern-recognition control of multifunctional upper-limb prostheses", Journal of Rehabilitation Research and Development, 2011, vol. 48, No. 6, pp. 619-628 <DOI:10.1682/JRRD.2010.08.0149>.

Singh, R. et al., "Trends and Challenges in EMG Based Control Scheme of Exoskeleton Robots- A Review", International Journal of Scientific & Engineering Research, Aug. 2012, vol. 3, No. 8, 8 pages.

Smith, L. et al., "Determining the Optimal Window Length for Pattern Recognition-Based Myoelectric Control: Balancing the Competing Effects of Classification Error and Controller Delay", IEEE Transactions on Neural Systems and Rehabilitation Engineering, Apr. 2011 (date of publication: Dec. 2010), vol. 19, No. 2, pp. 186-192 <DOI:10.1109/TNSRE.2010.2100828>.

Smith, L. et al., "Real-time simultaneous and proportional myoelectric control using intramuscular Emg", Journal of Neural Engineering, Nov. 2014, vol. 11, No. 6, article 066013, 13 pages. <DOI:10.1088/1741-2560/11/6/066013>.

Soechting, J. et al., "An assessment of the existence of muscle synergies during load perturbations and intentional movements of the human arm", Experimental Brain Research, Feb. 1989, vol. 74, No. 3, pp. 535-548 <DOI:10.1007/BF00247355>.

Soukoreff, R. et al., "Towards a standard for pointing device evaluation, perspectives on 27 years of Fitts' law research in HCI", International Journal of Human-Computer Studies, Dec. 2004 (available online Nov. 2004), vol. 61, No. 6, pp. 751-789 <DOI:10.1016/j.ijhcs.2004.09.001>.

Staudenmann, D. et al., "Independent Component Analysis of High-Density Electromyography in Muscle Force Estimation", IEEE Transactions on Biomedical Engineering, Apr. 2007 (date of publication: Mar. 2007), vol. 54, No. 4, pp. 751-754 <DOI:10.1109/TBME.2006.889202>.

Staudenmann, D. et al., "Methodological aspects of SEMG recordings for force estimation — A tutorial and review", Journal of Electromyography and Kinesiology, Jun. 2010 (available online: Sep. 2009), vol. 20, No. 3, pp. 375-387 <DOI:10.1016/j.jelekin.2009.08.005>.

Steele, K. et al., "The number and choice of muscles impact the results of muscle synergy analyses", Frontiers in Computational Neuroscience, Aug. 2013, vol. 7, article 105, pp. 1-9 <DOI:10.3389/fncom.2013.00105>.

Stegeman, D. et al., "Chapter 20 Multi-channel surface EMG in clinical neurophysiology", Supplements to Clinical Neurophysiology, 2000 (available online May 2009), vol. 53, pp. 155-162 <DOI:10.1016/S1567-424X(09)70151-5>.

(56) References Cited

OTHER PUBLICATIONS

Steuer, R. et al., "The mutual information: Detecting and evaluating dependencies between variables", Bioinformatics, Oct. 2002, vol. 18, No. 2, pp. S231-S240 <DOI:10.1093/bioinformatics/18.suppl_2.S231>.

Ting, L. et al., "A Limited Set of Muscle Synergies for Force Control During a Postural Task", Journal of Neurophysiology, Jan. 2005, vol. 93, No. 1, pp. 609-613 <DOI:10.1152/jn.00681.2004>.

Ting, L. et al., "Chapter 5: Decomposing Muscle Activity in Motor TasksMethods and Interpretation", in Motor Control: Theories, Experiments, and Applications (Oxford University Press, New York), 2010, pp. 102-138 <DOI:10.1093/acprof:oso/9780195395273.003.0005>.

Ting, L. et al., "Neuromechanics of muscle synergies for posture and movement", Current Opinion in Neurobiology, Dec. 2007 (available online Mar. 2008), vol. 17, No. 6, pp. 622-628 <DOI:10.1016/j.conb.2008.01.002>.

Tkach, D. et al., "Performance of pattern recognition myoelectric control using a generic electrode grid with Targeted Muscle Reinnervation patients", Annual International Conference of the IEEE Engineering in Medicine and Biology Society (San Diego, CA, Aug. 28-Sep. 1, 2012), 2012 (date added to IEEE Xplore: Nov. 2012), pp. 727-734 <DOI:10.1109/EMBC.2012.6346922>.

Tkach, D. et al., "Study of stability of time-domain features for electromyographic pattern recognition", Journal of and NeuroEngineering Rehabilitation, May 2010, vol. 7, No. 21, 13 pp. <DOI:10.1186/1743-0003-7-21>.

Torres-Oviedo, G. et al., "Muscle Synergies Characterizing Human Postural Responses", Journal of Neurophysiology, Oct. 2007, vol. 98, No. 4, pp. 2144-2156 <DOI:10.1152/jn.01360.2006>.

Torres-Oviedo, G. et al., "Muscle Synergy Organization Is Robust Across a Variety of Postural Perturbations", Journal of Neurophysiology, Sep. 2006, vol. 96, No. 3, pp. 1530-1546 <DOI:10.1152/jn.00810.2005>.

Tresch, M. et al., "Matrix Factorization Algorithms for the Identification of Muscle Synergies: Evaluation on Simulated and Experimental Data Sets", Journal of Neurophysiology, Apr. 2006, vol. 95, No. 4, pp. 2199-2212 <DOI:10.1152/jn.00222.2005>.

Tresch, M. et al., "The case for and against muscle synergies", Current Opinion in Neurobiology, Dec. 2009 (available online: Oct. 2009), vol. 19, No. 6, pp. 601-607 <DOI:10.1016/j.conb.2009.09.002>.

Tresch, M. et al., "The construction of movement by the spinal cord", Nature Neuroscience, Feb. 1999, vol. 2, pp. 162-167 <DOI:10.1038/5721>.

Tsuj, T. et al., "Bio-mimetic impedance control of an EMG-controlled prosthetic hand", IEEE/RSJ International Conference on Intelligent Robots and Systems (Takamatsu, Japan, Oct. 31-Nov. 5, 2000), 2000 (date added to IEEE Xplore: Aug. 2002), pp. 377-382 <DOI:10.1109/IROS.2000.894634>.

Ullah, K. et al., "A mathematical model for mapping EMG signal to joint torque for the human elbow joint using nonlinear regression", 4th International Conference on Autonomous Robots and Agents (Wellington, New Zealand, Feb. 10-12, 2009), 2009 (date added to IEEE Xplore: Mar. 2009), pp. 103-108 <DOI:10.1109/ICARA.2000.4803995>.

Vaca-Benitez, L. et al., "Exoskeleton Technology in Rehabilitation: Towards an EMG-Based Orthosis System for Upper Limb Neuromotor Rehabilitation", Journal of Robotics, Oct. 2013, vol. 2013, article 610589, 13 pages <DOI:10.1155/2013/610589>.

Valero-Cuevas, F. et al., "Structured Variability of Muscle Activations Supports the Minimal Intervention Principle of Motor Control", Journal of Neurophysiology, Jul. 2009, vol. 102, No. 1, pp. 59-68 <DOI:10.1152/jn.90324.2008>.

Van Dieën, J. et al., "The electro-mechanical delay of the erector spinae muscle: influence of rate of force development, fatigue and electrode location", European Journal of Applied Physiology and Occupational Physiology, Oct. 1991, vol. 63, No. 3-4, pp. 216-222 <DOI:10.1007/BF00233851>.

Vogel, J. et al., "Continuous robot control using surface electromyography of atrophic muscles", IEEE/RSJ International Conference on Intelligent Robots and Systems (Tokyo, Japan, Nov. 3-7, 2013), 2013 (date added to IEEE Xplore: Jan. 2014), pp. 845-850 <DOI:10.1109/IROS.2013.6696449>.

Vogel, J. et al., "EMG-based teleoperation and manipulation with the DLR LWR-III", IEEE/RSJ International Conference on Intelligent Robots and Systems (San Francisco, CA, Sep. 25-30, 2011), 2011 (date added to IEEE Xplore: Dec. 2011), pp. 672-678 <DOI:10.1109/IROS.2011.6094739>.

Walker, M. et al., "Practice with Sleep Makes Perfect: Sleep-Dependent Motor Skill Learning", Neuron, Jul. 2002, vol. 35, No. 1, pp. 205-211 <DOI:10.1016/50896-6273(02)00746-8>.

Weiss, E. et al., "Muscular and Postural Synergies of the Human Hand", Journal of Neurophysiology, Jul. 2004, vol. 92, No. 1, pp. 523-535 <DOI:10.1152/jn.01265.2003>.

Williams, M. et al., "Evaluation of Head Orientation and Neck Muscle EMG Signals as Command Inputs to a Human—Computer Interface for Individuals With High Tetraplegia", IEEE Transactions on Neural Systems and Rehabilitation Engineering, Oct. 2008 (date of publication: Sep. 2008), vol. 16, No. 5, pp. 485-496 <DOI:10.1109/TNSRE.2008.2006216>.

Willigenburg, N. et al., "Removing ECG contamination from EMG recordings: A comparison of ICA-based and other filtering procedures", Journal of Electromyography and Kinesiology, Jun. 2012 (available online Jan. 2012), vol. 22, No. 3, pp. 485-493 <DOI:10.1016/j.jelekin.2012.01.001>.

Willison, R., "A Method of Measuring Motor Unit Activity in Human Muscle", Journal of Physiology-London, 1963, vol. 168, No. 2, pp. 35-36.

Wolpaw, J. et al., "Brain—computer interfaces for communication and control", Clinical Neurophysiology, Jun. 2002 (available online: Apr. 2002), vol. 113, No. 6, pp. 767-791 <DOI:10.1016/51388-2457(02)00057-3>.

Wurth, S. et al., "A real time performance assessment of simultaneous pattern recognition control for multi-functional upper limb prostheses", 6th International IEEE/EMBS Conference on Neural Engineering (San Diego, CA, Nov. 6-8, 2013), 2013 (date added to IEEE Xplore: Jan. 2014), pp. 851-854 <DOI:10.1109/NER.2013.6696068>.

Wurth, S. et al., "Real-time comparison of conventional direct control and pattern recognition myoelectric control in a two-dimensional Fitts' law style test", Annual International Conference of the IEEE Engineering in Medicine and Biology Society (Osaka, Japan, Jul. 3-7, 2013), 2013 (date added to IEEE Xplore: Sep. 2013), pp. 3630-3633 <DOI:10.1109/EMBC.2013.6610329>.

Yatsenko, D. et al., "Simultaneous, Proportional, Multi-axis Prosthesis Control using Multichannel Surface EMG", 29th Annual International Conference of the IEEE Engineering in Medicine and Biology Society (Lyon, France, Aug. 22-26, 2007), 2007 (available online: Oct. 2007), pp. 6133-6136 <DOI:10.1109/IEMBS.2007.4353749>.

Yazici, I. et al., "Classification of EMG signals using wavelet based autoregressive models and neural networks to control prothesis-bionic hand", 14th National Biomedical Engineering Meeting (Balcova, Turkey, May 20-22, 2009), 2009 (date added to IEEE Xplore: Jun. 2009), pp. 1-4 <DOI:10.1109/BIYOMUT.2009.5130379>.

Young, A. et al., "A comparison of the real-time controllability of pattern recognition to conventional myoelectric control for discrete and simultaneous movements", Journal of NeuroEngineering and Rehabilitation, Jan. 2014, vol. 11, No. 5, 10 pages <DOI:10.1186/1743-0003-11-5>.

Young, A. et al., "A new hierarchical approach for simultaneous control of multi-joint powered prostheses", IEEE RAS & EMBS International Conference on Biomedical Robotics and Biomechatronics (Rome, Italy, Jun. 24-27, 2012), 2012 (date added to IEEE Xplore: Aug. 2012), pp. 514-520 <DOI:10.1109/BioRob.2012.6290709>.

Young, A. et al., "Classification of Simultaneous Movements Using Surface EMG Pattern Recognition", IEEE Transactions on Biomedical Engineering, May 2013 (date of publication: Dec. 2012), vol. 60, No. 5, pp. 1250-1258 <DOI:10.1109/TBME.2012.2232293>.

(56) References Cited

OTHER PUBLICATIONS

Young, A. et al., "The Effects of Electrode Size and Orientation on the Sensitivity of Myoelectric Pattern Recognition Systems to Electrode Shift", IEEE Transactions on Biomedical Engineering, Sep. 2011 (date of publication: Jun. 2011), vol. 58, No. 9, pp. 2537-2544 <DOI:10.1109/TBME.2011.2159216>.

Zajac, F., "Muscle and tendon: properties, models, scaling, and application to biomechanics and motor control", Critical Reviews in Biomedical Engineering, 1989, vol. 17, No. 4, pp. 359-411.

Zander, T. et al., "Towards passive brain-computer interfaces: applying brain-computer interface technology to human-machine systems in general", Journal of Neural Engineering, Mar. 2011, vol. 8, No. 2, article 025005, 5 pages <DOI:10.1088/1741-2560/8/2/025005>.

Zardoshti-Kermani, M. et al., "EMG feature evaluation for movement control of upper extremity prostheses", IEEE Transactions on Rehabilitation Engineering, Dec. 1995, vol. 3, No. 4, pp. 324-333 <DOI:10.1109/86.481972>.

Zazula, D. et al., "An approach to surface EMG decomposition based on higher-order cumulants", Computer Methods and Programs in Biomedicine, Dec. 2005 (available online: Mar. 2006), vol. 80, No. 1, pp. S51-S60 <DOI:10.1016/S0169-2607(05)80006-9>.

Zecca, M. et al., "Control of multifunctional prosthetic hands by processing the electromyographic signal", Critical Reviews in Biomedical Engineering, 2002, vol. 30, No. 4-6, pp. 459-485.

Zhang, F. et al., "SEMG feature extraction methods for pattern recognition of upper limbs", International Conference on Advanced Mechatronic Systems (Zhengzhou, China, Aug. 11-13, 2011), 2011 (date added to IEEE Xplore: Sep. 2011), pp. 222-227.

Zhang, Q. et al., "FES-Induced Torque Prediction With Evoked EMG Sensing for Muscle Fatigue Tracking", IEEE/ASME Transactions on Mechatronics, Oct. 2011 (date of publication: Jul. 2011), vol. 16, No. 5, pp. 816-826 <DOI:10.1109/TMECH.2011.2160809>.

Zhang, X. et al., "A real-time, practical sensor fault-tolerant module for robust EMG pattern recognition", Journal of NeuroEngineering and Rehabilitation, Feb. 2015, vol. 12, No. 18, 16 pages <DOI:10.1186/s12984-015-0011-y>.

Zhao, J. et al., "Levenberg-Marquardt Based Neural Network Control for a Five-fingered Prosthetic Hand", IEEE International Conference on Robotics and Automation (Barcelona, Spain, Apr. 18-22, 2005), 2005 (date added to IEEE Xplore: Jan. 2006), pp. 4482-4487 <DOI:10.1109/ROBOT.2005.1570810>.

Zhong, J. et al., "Recognition of hand motions via surface EMG signal with rough entropy", Annual International Conference of the IEEE Engineering in Medicine and Biology Society (Boston, MA, Aug. 30-Sep. 3, 2011), 2011 (available online: Dec. 2011), pp. 4100-4103 <DOI:10.1109/IEMBS.2011.6091018>.

Zhu, C. et al., "Power assistance for human elbow motion support using minimal EMG signals with admittance control", IEEE International Conference on Mechatronics and Automation (Beijing, China, Aug. 7-10, 2011), 2011 (date added to IEEE Xplore: Aug. 2011), pp. 276-281 <DOI:10.1109/ICMA.2011.5985670>.

Zwarts, M. et al., "Multichannel surface EMG: Basic aspects and clinical utility", Muscle & Nerve, Jul. 2003 (available online Apr. 2003), vol. 28, No. 1, pp. 1-17 <DOI:10.1002/mus.10358>.

U.S. Appl. No. 16/342,764.

Castellini, C. et al., "Evidence of muscle synergies during human grasping", Biological Cybernetics, Apr. 2013 (available online: Jan. 2013), vol. 107, No. 2, pp. 233-245 <DOI:10.1007/s00422-013-0548-4>.

Castellini, C. et al., "Fine detection of grasp force and posture by amputees via surface electromyography", Journal of Physiology-Paris, May-Sep. 2009 (available online: Aug. 2009), vol. 103, No. 3-5, pp. 255-262 <DOI:10.1016/j.jphysparis.2009.08.008>.

Castellini, C. et al., "Multi-subject/daily-life activity EMG-based control of mechanical hands", Journal of NeuroEngineering and Rehabilitation, Nov. 2009, vol. 6, No. 41, pp. 1-11 <DOI:10.1186/1743-0003-6-41>.

Castellini, C. et al., "Proceedings of the first workshop on Peripheral Machine Interfaces: going beyond traditional surface electromyography", Frontiers in Neurorobotics, Aug. 2014, vol. 8, No. 22, 17 pages <DOI:10.3389/fnbot.2014.00022>.

Cavallaro, E. et al., "Real-Time Myoprocessors for a Neural Controlled Powered Exoskeleton Arm", IEEE Transactions on Biomedical Engineering, Nov. 2006 (available online: Oct. 2006), vol. 53, No. 11, pp. 2387-2396 <DOI:10.1109/TBME.2006.880883>.

Cavanagh, P. et al., "Electromechanical delay in human skeletal muscle under concentric and eccentric contractions", European Journal of Applied Physiology and Occupational Physiology, Nov. 1979, vol. 42, No. 3, pp. 159-163.

Chan, A. et al., "Continuous myoelectric control for powered prostheses using hidden Markov models", IEEE Transactions on Biomedical Engineering, Jan. 2005 (date of publication: Dec. 2004), vol. 52, No. 1, pp. 121-124 <DOI:10.1109/TBME.2004.836492>.

Chanaud, C. et al., "Functionally complex muscles of the cat hindlimb", Experimental Brain Research, Jun. 1991, vol. 85, No. 2, pp. 300-313.

Chase, S. et al., "Bias, optimal linear estimation, and the differences between open-loop simulation and closed-loop performance of spiking-based brain—computer interface algorithms", Neural Networks, Nov. 2009 (available online: May 2009), vol. 22, No. 9, pp. 1203-1213 <DOI:10.1016/j.neunet.2009.05.005>.

Chen, L. et al., "Electromyogram signal analysis and movement recognition based on wavelet packet transform", International Conference on Information and Automation (Zhuhai, China, Jun. 22-24, 2009), 2009 (Date added to IEEE Xplore: Aug. 2009), pp. 1482-1487 <DOI:10.1109/ICINFA.2009.5205151>.

Chen, X. et al., "A discriminant bispectrum feature for surface electromyogram signal classification", Medical Engineering & Physics, Mar. 2010 (available online: Dec. 2009), vol. 32, No. 2, pp. 126-135 <DOI:10.1016/j.medengphy.2009.10.016>.

Marchal-Crespo, L. et al., "Review of control strategies for robotic movement training after neurologic injury", Journal of NeuroEngineering and Rehabilitation, Jun. 2009, vol. 6, No. 20, 15 pages. <DOI:10.1186/1743-0003-6-20>.

Matsubara, T. et al., "Bilinear Modeling of EMG Signals to Extract User-Independent Features for Multiuser Myoelectric Interface", IEEE Transactions on Biomedical Engineering, Aug. 2013 (date of publication: Mar. 2013), vol. 60, No. 8, pp. 2205-2213 <DOI:10.1109/TBME.2013.2250502>.

Matsumoto, Y. et al., "Tremor frequency based filter to extract voluntary movement of patients with essential tremor", 4th IEEE RAS & EMBS International Conference on Biomedical Robotics and Biomechantronics (Rome, Italy, Jun. 24-27, 2012), 2012 (date added to IEEE Xplore: Aug. 2012), pp. 1415-1422 <DOI:10.1109/BioRob.2012.6290905>.

McFarland, D. et al., "Brain-computer interfaces for communication and control", Communications of the ACM Magazine, May 2011, vol. 54, No. 5, pp. 60-66 <DOI:10.1145/1941487.1941506>.

Meek, S. et al., "Comparison of signal-to-noise ratio of myoelectric filters for prosthesis control", Journal of Rehabilitation Research and Development, 1992, vol. 29, No. 4, pp. 9-20 <DOI:10.1682/JRRD.1992.10.0009>.

Meng, M. et al., "EMG signals based gait phases recognition using hidden Markov models", IEEE International Conference on Information and Automation (Harbin, China, Jun. 20-23, 2010), 2010 (date added to IEEE Xplore: Jul. 2010), pp. 852-856 <DOI:10.1109/ICINFA.2010.5512456>.

Merletti, R. et al., "The linear electrode array: a useful tool with many applications", Journal of Electromyography and Kinesiology, Feb. 2003 (available online Dec. 2002), vol. 13, No. 1, pp. 37-47 <DOI:10.1016/S1050-6411(02)00082-2>.

Mesin, L. et al., "Effect of spatial filtering on crosstalk reduction in surface EMG recordings", Medical Engineering & Physics, Apr. 2009 (available online Jun. 2008), vol. 31, No. 3, pp. 374-383 <DOI:10.1016/j.medengphy.2008.05.006>.

Micera, S. et al., "A hybrid approach to EMG pattern analysis for classification of arm movements using statistical and fuzzy techniques", Medical Engineering & Physics, Jun. 1999 (available online Sep. 1999), vol. 21, No. 5, pp. 303-311 <DOI:10.1016/51350-4533(99)00055-7>.

(56) References Cited

OTHER PUBLICATIONS

Millán, J., "Brain—Computer Interfaces", Introduction to Neural Engineering for Motor Rehabilitation, Jul. 2013, vol. pp. 237-253 <DOI:10.1002/9781118628522.ch12>.

Miller, L. et al., "Improved Myoelectric Prosthesis Control Using Targeted Reinnervation Surgery: A Case Series", IEEE Transactions on Neural Systems and Rehabilitation Engineering, Feb. 2008, vol. 16, No. 1, pp. 46-50 <DOI:10.1109/TNSRE.2007.911817>.

Miller, L. et al., "Summary and Recommendations of the Academy's State of the Science Conference on Upper Limb Prosthetic Outcome Measures", Journal of Prosthetics and Orthotics, Oct. 2009, vol. 21, No. 9, pp. P83-P89 <DOI:10.1097/JPO.0b013e3181ae974d>.

Chen, X. et al., "Application of a self-enhancing classification method to electromyography pattern recognition for multifunctional prosthesis control", Journal of NeuroEngineering and Rehabilitation, May 2013, vol. 10, No. 44, 13 pages <DOI:10.1186/1743-0003-10-44>.

Cheung, V. et al., "Muscle synergy patterns as physiological markers of motor cortical damage", Proceedings of the National Academy of Sciences, Sep. 2012 (available online: Aug. 2012), vol. 109, No. 36, pp. 14652-14656 <DOI:10.1073/pnas.1212056109>.

Chiel, H. et al., "The Brain in Its Body: Motor Control and Sensing in a Biomechanical Context", The Journal of Neuroscience, Oct. 2009, vol. 29, No. 41, pp. 12807-12814 <DOI:10.1523/JNEUROSCI.3338-09.2009>.

Choi, C. et al., "A Real-time EMG-based Assistive Computer Interface for the Upper Limb Disabled", IEEE 10th Conference on Rehabilitation Robotics (Noordwijk, Netherlands, Jun. 13-15, 2007), 2007 (Date added to the IEEE Xplore: Jan. 2008), pp. 459-462 <DOI:10.1109/ICORR.2007.4428465>.

Choi, C. et al., "Synergy matrices to estimate fluid wrist movements by surface electromyography", Medical Engineering & Physics, Oct. 2011 (available online: Mar. 2011), vol. 33, No. 8, pp. 916-923 <DOI:10.1016/j.medengphy.2011.02.006>.

Chong, Y. et al., "A study of back-propagation and radial basis neural network on EMG signal classification", 6th International Symposium on Mechatronics and its Applications (Sharjah, United Arab Emiratees, Mar. 23-26, 2009), 2009 (Date added to IEEE Xplore: Jul. 2009), pp. 1-6 <DOI:10.1109/ISMA.2009.5164797>.

Chu, J-U. et al., "Control of multifunction myoelectric hand using a real-time EMG pattern recognition", IEEE/RSJ International Conference on Intelligent Robots and Systems (Edmonton, Canada, Aug. 2-6, 2005), 2005 (Date added to IEEE Xplore: Dec. 2005), 6 pages <DOI:10.1109/IROS.2005.1545586>.

Cipriani, C. et al., "Dexterous Control of a Prosthetic Hand Using Fine-Wire Intramuscular Electrodes in Targeted Extrinsic Muscles", IEEE Transactions on Neural Systems and Rehabilitation Engineering, Jul. 2014 (date of publication: Jan. 2014), vol. 22, No. 4, pp. 828-836 <DOI:10.1109/TNSRE.2014.2301234>.

Cipriani, C. et al., "On the Shared Control of an EMG-Controlled Prosthetic Hand: Analysis of User-Prosthesis Interaction", IEEE Transactions on Robotics, Feb. 2008, vol. 24, No. 1, pp. 170-184 <DOI:10.1109/TRO.2007.910708>.

Clancy, E. et al., "Identification of Constant-Posture EMG-Torque Relationship About the Elbow Using Nonlinear Dynamic Models", IEEE Transactions on Biomedical Engineering, Jan. 2012 (date of publication: Oct. 2011), vol. 59, No. 1, pp. 205-212 <DOI:10.1109/TBME.2011.2170423>.

Clancy, E. et al., "Sampling, noise-reduction and amplitude estimation issues in surface electromyography", Journal of Electromyography and Kinesiology, Feb. 2002, vol. 12, No. 1, pp. 1-16 <DOI:10.1016/S1050-6411(01)00033-5>.

Clark, D. et al., "Merging of Healthy Motor Modules Predicts Reduced Locomotor Performance and Muscle Coordination Complexity Post-Stroke", Journal of Neurophysiology, Feb. 2010, vol. 103, No. 2, pp. 844-857 <DOI:10.1152/jn.00825.2009>.

Clingman, R. et al., "A Novel Myoelectric Training Device for Upper Limb Prostheses", IEEE Transactions on Neural Systems and Rehabilitation Engineering, Jul. 2014 (date of publication: Apr. 2014), vol. 22, No. 4, pp. 879-885 <DOI:10.1109/TNSRE.2014.2315046>.

D'Avella, a. et al., "Control of Fast-Reaching Movements by Muscle Synergy Combinations", The Journal of Neuroscience, Jul. 2006, vol. 26, No. 30, pp. 7791-7810 <DOI:10.1523/JNEUROSCI.0830-06.2006>.

D'Avella, A. et al., "Shared and specific muscle synergies in natural motor behaviors", Proceedings of the National Academy of Sciences of the United States of America, Feb. 2005, vol. 102, No. 8, pp. 3076-3081 <DOI:10.1073/PNAS.0500199102>.

Davoodi, R. et al., "Development of a physics-based target shooting game to train amputee users of multijoint upper limb prostheses", Presence: Teleoperators and Virtual Environments, Winter 2012 (available online: May 2012), vol. 21, No. 1, pp. 85-95 <DOI:10.1162/PRES_a_00091>.

De La Rosa, R. et al., "Myo-Pong: A neuromuscular game for the UVa-Neuromuscular Training System platform", Virtual Rehabilitation (Vancouver, Canada, Aug. 25-27, 2008), 2008 (Date added to IEEE Xplore: Sep. 2008), p. 61 <DOI:10.1109/ICVR.2008.4625124>.

De Rugy, A. et al., "Are muscle synergies useful for neural control?", Frontiers in Computational Neuroscience, Mar. 2013, vol. 7, No. 19, 13 pages <DOI:10.3389fincom.2013.00019>.

De Rugy, a. et al., "Muscle Coordination Is Habitual Rather than Optimal", Journal of Neuroscience, May 2012, vol. 32, No. 21, pp. 7384-7391 <DOI:10.1523/JNEUROSCI.5792-11.2012>.

Delis, I. et al., "Quantitative evaluation of muscle synergy models: a single-trial task decoding approach", Frontiers in Computational Neuroscience, Feb. 2013, vol. 7, No. 8, 21 pp. <DOI:10.3389/fncom.2013.00008>.

Dimitrov, G. et al., "Simulation analysis of the ability of different types of multi-electrodes to increase selectivity of detection and to reduce cross-talk", Journal of Electromyography and Kinesiology, Apr. 2003, vol. 13, No. 2, pp. 125-138 <DOI:10.1016/S1050-6411(02)00095-0>.

Ding, Q. et al., "A Novel Motion Estimate Method of Human Joint with EMG-Driven Model", 5th International Conference on Bioinformatics and Biomedical Engineering (Wuhan, China, May 10-12, 2011), 2011, 5 pages <DOI:10.1109/icbbe.2011.5780185>.

Drost, G. et al., "Clinical applications of high-density surface EMG: A systematic review", Journal of Electromyography and Kinesiology, Dec. 2006, vol. 16, No. 6, pp. 586-602 <DOI:10.1016/j.jelekin.2006.09.005>.

Drost, G. et al., "Motor unit characteristics in healthy subjects and those with postpoliomyelitis syndrome: a high-density surface EMG study", Muscle & Nerve, Sep. 2004 (available online: Jul. 2004), vol. 30, No. 3, pp. 269-276 <DOI:10.1002/mus.20104>.

Du, S. et al., "Temporal vs. spectral approach to feature extraction from prehensile EMG signals", IEEE International Conference on Information Reuse and Integration (Las Vegas, NV, Nov. 8-10, 2004), 2004 (Date added to IEEE Xplore: May 2005), pp. 344-350 <DOI:10.1109/IRI.2004.1431485>.

El-Daydamony, E. et al., "A computerized system for SEMG signals analysis and classification", National Radio Science Conference (Tanta, Egypt, Mar. 18-20, 2008), 2008 (Date added to IEEE Xplore: Jun. 2008), 7 pages <DOI:10.1109/NRSC.2008.4542388>.

Englehart, K. et al., "A wavelet-based continuous classification scheme for multifunction myoelectric control", IEEE Transactions on Biomedical Engineering, Mar. 2001, vol. 48, No. 3, pp. 302-311 <DOI:10.1109/10.914793>.

Englehart, K. et al., "Classification of the myoelectric signal using time-frequency based representations", Medical Engineering & Physics, Jul. 1999, vol. 21, No. 6-7, pp. 431-438 <DOI:10.1016/S1350-4533(99)00066-1>.

Erkilinc, M. et al., "Camera control with EMG signals using Principal Component Analysis and support vector machines", IEEE International Systems Conference (Montreal, Canada, Apr. 4-7, 2011), 2011 (Date added to IEEE Xplore: Jun. 2011), 5 pages <DOI:10.1109/SYSCON.2011.5929070>.

Farina, D. et al., "Biophysics of the Generation of EMG Signals", in: Merletti, R. (ed.) "Electromyography: Physiology, Engineering,

(56) References Cited

OTHER PUBLICATIONS and Noninvasive Applications", Chapter 4, (John Wiley & Sons, Hoboken, NJ, Jul. 2004), pp. 81-105 <DOI:10.1002/0471678384.ch4>.
Farina, D. et al., "Comparison of algorithms for estimation of EMG variables during voluntary isometric contractions", Journal of Electromyography and Kinesiology, Oct. 2000 (available online Sep. 2000), vol. 10, No. 5, pp. 337-349 <DOI:10.1016/S1050-6411(00)00025-0>.
Farina, D. et al., "High-density EMG E-Textile systems for the control of active prostheses", IEEE Engineering in Medicine and Biology (Buenos Aires, Argentina, Aug. 31-Sep. 4, 2010), 2010 (Date added to IEEE Xplore: Nov. 2010), pp. 3591-3593 <DOI:10.1109/IEMBS.2010.5627455>.
Farina, D. et al., "Methods for estimating muscle fibre conduction velocity from surface electromyographic signals", Medical and Biological Engineering and Computing, Jul. 2004, vol. 42, No. 4, pp. 432-445 <DOI:10.1007/BF02350984>.
Farina, D. et al., "Surface EMG crosstalk between knee extensor muscles: Experimental and model results", Muscle & Nerve, Nov. 2002 (available online: Sep. 2002), vol. 26, No. 5, pp. 681-695 <DOI:10.1002/mus.10256>.
Farina, D. et al., "The Extraction of Neural Information from the Surface EMG for the Control of Upper-Limb Prostheses: Emerging Avenues and Challenges", IEEE Transactions on Neural Systems and Rehabilitation Engineering, Jul. 2014 (available online: Feb. 2014), vol. 22, No. 4, pp. 797-809 <DOI:10.1109/TNSRE.2014.2305111>.
Farina, D., "Interpretation of the surface electromyogram in dynamic contractions", Exercise and Sport Sciences Reviews, Jul. 2006, vol. 34, No. 3, pp. 121-127.
Felzer, T. et al., "HaWCoS: The "Hands-free" Wheelchair Control System", Proceedings of the 5th International ACM Conference on Assistive Technologies (Edinburgh, Scotland, Jul. 8-10, 2002), 2002, pp. 127-134 <DOI:10.1145/638249.638273>.
Finley, F. et al., "Myocoder studies of multiple myopotential response", Archives of Physical Medicine and Rehabilitation, Nov. 1967, vol. 48, No. 11, pp. 598-601.
Fleischer, C. et al., "Predicting the intended motion with EMG signals for an exoskeleton orthosis controller", IEEE/RSJ International Conference on Intelligent Robots and Systems (Edmonton, Canada, Aug. 2-6, 2005), 2005 (date added to IEEE Xplore: Dec. 2005), 6 pages <DOI:10.1109/IROS.2005.1545504>.
Fougner, A. et al., "Control of Upper Limb Prostheses: Terminology and Proportional Myoelectric Control—A Review", IEEE Transactions on Neural Systems and Rehabilitation Engineering, Sep. 2012 (available online May 2012), vol. 20, No. 5, pp. 663-677 <DOI:10.1109/TNSRE.2012.2196711>.
Fougner, A. et al., "Resolving the Limb Position Effect in Myoelectric Pattern Recognition", IEEE Transactions on Neural Systems and Rehabilitation Engineering, Dec. 2011 (available online Aug. 2011), vol. 19, No. 6, pp. 644-651 <DOI:10.1109/TNSRE.2011.2163529>.
Fukuda, O. et al., "A human-assisting manipulator teleoperated by EMG signals and arm motions", IEEE Transactions on Robotics and Automation, Apr. 2003, vol. 19, No. 2, pp. 210-222 <DOI:10.1109/TRA.2003.808873>.
Gallant, P. et al., "Feature-based classification of myoelectric signals using artificial neural networks", Medical and Biological Engineering and Computing, Jul. 1998, vol. 36, No. 4, pp. 485-489 <DOI:10.1007/BF02523219>.
Gallina, A. et al., "Innervation zone of the vastus medialis muscle: position and effect on surface EMG variables", Physiological Measurement, Sep. 2013, vol. 34, No. 11, pp. 1411-1422 <DOI:10.1088/0967-3334/34/11/1411>.
Gallina, A. et al., "Uneven spatial distribution of surface EMG: what does it mean?", European Journal of Applied Physiology, Apr. 2013 (available online: Sep. 2012), vol. 113, No. 4, pp. 887-894 <DOI:10.1007/s00421-012-2498-2>.
Geng, Y. et al., "Reduction of the effect of arm position variation on real-time performance of motion classification", IEEE Engineering in Medicine and Biology Society (San Diego, CA, Aug. 28-Sep. 1, 2012), 2012 (Date added to IEEE Xplore: Nov. 2012), pp. 2772-2775 <DOI:10.1109/EMBC.2012.6346539>.
Gibson, A. et al., "User-Independent Hand Motion Classifcation with Electromyography", ASME 2013 Dynamic Systems and Control Conference (Palo Alto, CA, Oct. 21-23, 2013), 2013, 6 pages <DOI:10.1115/DSCC2013-3832>.
Gijsberts, A. et al., "Stable myoelectric control of a hand prosthesis using non-linear incremental learning", Frontiers in Neurorobotics, Feb. 2014, vol. 8, No. 8, 15 pages <DOI:10.3389/fnbot.2014.00008>.
Gillis, L., "Recent advances in the treatment of arm amputations, kineplastic surgery and arm prostheses", Annals of the Royal College of Surgeons of England, Mar. 1948, vol. 3, No. 5, pp. 227-245.
Gonzalez-Izal, M. et al., "EMG spectral indices and muscle power fatigue during dynamic contractions", Journal of Electromyography and Kinesiology, Apr. 2010 (available online Apr. 2009), vol. 20, No. 2, pp. 233-240 <DOI:10.1016/j.jelekin.2009.03.011>.
Abellaneda, S. et al., "The relative lengthening of the myotendinous structures in the medial gastrocnemius during passive stretching differs among individuals", Journal of Applied Physiology, Jan. 2009, vol. 106, No. 1, pp. 169-177 <DOI:10.1152/japplphysiol.90577.2008>.
Ahmad, I. et al., "A review of EMG recording technique", International Journal of Engineering Science and Technology, Feb. 2012, vol. 4, No. 2, pp. 530-539.
Ahsan, R. Md. et al., "VHDL Modelling of Fixed-point DWT for the Purpose of EMG Signal Denoising", Third International Conference on Computational Intelligence, Communication Systems and Networks (Bali, Indonesia, Jul. 26-28, 2011), 2011 (Date added to IEEE Xplore: Aug. 2011), pp. 236-241 <DOI:10.1109/CICSyN.2011.58>.
Ajiboye, A. et al., "A heuristic fuzzy logic approach to EMG pattern recognition for multifunctional prosthesis control", IEEE Transactions on Neural Systems and Rehabilitation Engineering, Sep. 2005, vol. 13, No. 3, pp. 280-291 <DOI:10.1109/TNSRE.2005.847357>.
Ajiboye, A. et al., "Muscle synergies as a predictive framework for the EMG patterns of new hand postures", Journal of Neural Engineering, May 2009, vol. 6, No. 3, article 036004, 15 pages <DOI:10.1088/1741-2560/6/3/036004>.
Ajoudani, A. et al., "Exploring Teleimpedance and Tactile Feedback for Intuitive Control of the Pisa/IIT SoftHand", IEEE Transactions on Haptics, Apr.-Jun. 2014, vol. 7, No. 2, pp. 203-215 <DOI:10.1109/TOH.2014.2309142>.
Ajoudani, A. et al., "Teleimpedance control of a synergy-driven anthropomorphic hand", IEEE/RSJ International Conference on Intelligent Robots and Systems (Tokyo, Japan, Nov. 3-7, 2013), 2013 (Date added to IEEE Xplore: Jan. 2014), 1985-1991 <DOI:10.1109/IROS.2013.6696620>.
Ajoudani, A. et al., "Tele-impedance: Teleoperation with impedance regulation using a body-machine interface", The International Journal of Robotics Research, Oct. 2012, vol. 31, No. 13, pp. 1642-1656 <DOI:10.1177/0278364912464668>.
Ameri, A. et al., "Real-Time, Simultaneous Myoelectric Control Using Force and Position-Based Training Paradigms", IEEE Transactions on Biomedical Engineering, Feb. 2014, vol. 61, No. 2, pp. 279-287 <DOI:10.1109/TBME.2013.2281595>.
Amsuss, S. et al., "Self-Correcting Pattern Recognition System of Surface EMG Signals for Upper Limb Prosthesis Control", IEEE Transactions on Biomedical Engineering, Apr. 2014, vol. 61, No. 4, pp. 1167-1176 <DOI:10.1109/TBME.2013.2296274>.
Anderson, F. et al., "Augmented reality improves myoelectric prosthesis training", International Journal on Disability and Human Development, Aug. 2014, vol. 13, No. 3, pp. 349-354 <DOI:10.1515/ijdhd-2014-0327>.
Andrade, A. et al., "On the relationship between features extracted from EMG and force for constant and dynamic protocols", IEEE Engineering in Medicine and Biology Society (San Diego, CA, Aug. 28-Sep. 1, 2012), 2012 (date added to IEEE Xplore: Nov. 2012), pp. 3392-3395 <DOI:10.1109/EMBC.2012.6346693>.
Antuvan, C. et al., "Embedded human control of robots using myoelectric interfaces", IEEE Transactions on Neural Systems and

(56) References Cited

OTHER PUBLICATIONS

Rehabilitation Engineering, Jul. 2014 (date of publication: Jan. 2014), vol. 22, No. 4, pp. 820-827 <DOI:10.1109/TNSRE.2014.2302212>.

Armiger, R. et al., "Air-guitar hero: a real-time video game interface for training and evaluation of dexterous upper-extremity neuroprosthetic control algorithms", IEEE Biomedical Circuits and Systems Conference (Baltimore, MD, Nov. 20-22, 2008), 2008 (Date added to IEEE Xplore: Feb. 2009), pp. 121-124 <DOI:10.1109/BIOCAS.2008.4696889>.

Artemiadis, P. et al., "A biomimetic approach to inverse kinematics for a redundant robot arm", Autonomous Robots, Nov. 2010 (available online Jun. 2010), vol. 29, No. 3-4, pp. 293-308 <DOI:10.1007/s10514-010-9196-x>.

Artemiadis, P. et al., "A Switching Regime Model for the EMG-Based Control of a Robot Arm", IEEE Transactions on Systems, Man, and Cybernetics, Part B (Cybernetics), Feb. 2011 (date of publication: Apr. 2010), vol. 41, No. 1, pp. 53-63 <DOI:10.1109/TSMBC.2010.2045120>.

Artemiadis, P. et al., "An EMG-Based Robot Control Scheme Robust to Time-Varying EMG Signal Features", IEEE Transactions on Information Technology in Biomedicine, May 2010 (date of publication: Feb. 2010), vol. 14, No. 3, pp. 582-588 <DOI:10.1109/TITB.2010.2040832>.

Artemiadis, P. et al., "EMG-Based Control of a Robot Arm Using Low-Dimensional Embeddings", IEEE Transactions on Robotics, Apr. 2010 (date of publication: Jan. 2010), vol. 26, No. 2, pp. 393-398 <DOI:10.1109/TRO.2009.2039378>.

Artemiadis, P. et al., "EMG-Based Position and Force Estimates in Coupled Human-Robot Systems: Towards EMG-Controlled Exoskeletons", Experimental Robotics, 2009, vol. 54, pp. 241-250 <DOI:10.1007/978-3-642-00196-3>.

Artemiadis, P. et al., "EMG-based teleoperation of a robot arm in planar catching movements using Armax model and trajectory monitoring techniques", IEEE International Conference on Robotics and Automation (Orlando, FL, May 15-19, 2006), 2006 (Date added to IEEE Xplore: Jun. 2006), pp. 3244-3249 <DOI:10.1109/ROBOT.2006.1642196>.

Artemiadis, P. et al., "Teleoperation of a robot manipulator using EMG signals and a position tracker", IEEE/RSJ International Conference on Intelligent Robots and Systems (Edmonton, Canada, Aug. 2-6, 2005), 2005 (Date added to IEEE Xplore: Dec. 2005), pp. 1003-1008 <DOI:10.1109/IROS.2005.1545509>.

Assad, C. et al., "BioSleeve: A natural EMG-based interface for HRI", ACM/IEEE International Conference on Human-Robot Interaction (Tokyo, Japan, Mar. 3-6, 2013), 2013, pp. 69-70 <DOI:10.1109/HRI.2013.6483505>.

Atkins, D. et al., "Epidemiologic overview of individuals with upper-limb loss and their reported research priorities", Journal of Prosthetics and Orthotics, Winter 1996, vol. 8, No. 1, pp. 2-11.

Atzori, M. et al., "Building the Ninapro database: A resource for the biorobotics community", IEEE RAS/EMBS International Conference on Biomedical Robotics and Biomechatronics (Roma, Italy, Jun. 24-27, 2012), 2012 (Date added to IEEE Xplore: Aug. 2012), pp. 1258-1265 <DOI:10.1109/BioRob.2012.6290287>.

Atzori, M. et al., "Electromyography data for non-invasive naturally-controlled robotic hand prostheses", Scientific Data, Dec. 2014, vol. 1, No. 140053, 13 pages. <DOI:10.1038/sdata.2014.53>.

Aukes, D. et al., "Selectively compliant underactuated hand for mobile manipulation", IEEE International Conference on Robotics and Automation (St. Paul, MN, May 14-18, 2012), 2012 (Date added to IEEE Xplore: Jun. 2012), pp. 2824-2829 <DOI:10.1109/ICRA.2012.6224738>.

Baker, J. et al., "Continuous Detection and Decoding of Dexterous Finger Flexions With Implantable MyoElectric Sensors", IEEE Transactions on Neural Systems and Rehabilitation Engineering, Aug. 2010 (date of publication: Apr. 2010), vol. 18, No. 4, pp. 424-432 <DOI:10.1109/TNSRE.2010.2047590>.

Baspinar, U. et al., "Classification of hand movements by using artificial neural network", International Symposium on innovations in Intelligent Systems and Applications (Trabzon, Turkey, Jul. 2-4, 2012), 2012, pp. 1-4 <DOI:10.1109/INISTA.2012.6247014>.

Berger, D. et al., "Effective force control by muscle synergies", Frontiers in Computational Neuroscience, Apr. 2014, vol. 8, No. 46, 13 pp. <DOI:10.3389/fncom.2014.00046>.

Berniker, M. et al., "Simplified and effective motor control based on muscle synergies to exploit musculoskeletal dynamics", Proceedings of the National Academy of Sciences, May 2009 (available online: Apr. 2009), vol. 106, No. 18, pp. 7601-7606 <DOI:10.1073/pnas.0901512106>.

Bilodeau, M. et al., "Normality and stationarity of EMG signals of elbow flexor muscles during ramp and step isometric contractions", Journal of Electromyography and Kinesiology, Jun. 1997, vol. 7, No. 2, pp. 87-96 <DOI:10.1016/51050-6411(96)00024-7>.

Bitzer, S. et al., "Learning EMG control of a robotic hand: towards active prostheses", IEEE International Conference on Robotics and Automation (Orlando, FL, May 15-19, 2006), 2006 (Date added to IEEE Xplore: Jun. 2006), pp. 2819-2823 <DOI:10.1109/ROBOT.2006.1642128>.

Blank, A. et al., "Task-dependent impedance and implications for upper-limb prosthesis control", The International Journal of Robotics Research, Feb. 2014, vol. 33, No. 6, pp. 827-846 <DOI:10.1177/0278364913517728>.

Boschmann, A. et al., "Development of a Pattern Recognition-Based Myoelectric Transhumeral Prosthesis with Multifunctional Simultaneous Control Using a Model-Driven Approach for Mechatronic Systems", MyoElectric Controls/Powered Prosthetics Symposium (New Brunswick, Canada, Aug. 14-19, 2011), 2011, 4 pages.

Brewer, B. et al., "Poststroke Upper Extremity Rehabilitation: A Review of Robotic Systems and Clinical Results", Topics in Stroke Rehabilitation, Nov. 2007, vol. 14, No. 6, pp. 22-44 <DOI:10.1310/tsr1406-22>.

Burkholder, T. et al., "Practical limits on muscle synergy identification by non-negative matrix factorization in systems with mechanical constraints", Medical & Biological Engineering & Computing, Feb. 2013 (available online: Nov. 2012), vol. 51, No. 1-2, pp. 187-196 <DOI:10.1007/s11517-012-0983-8>.

Carmena, J., "Advances in neuroprosthetic learning and control", PLoS Biology, May 2013, vol. 11, No. 5, article e1001561, 4 pages <DOI:10.1371/journal.pbio.1001561>.

Carrozza, M. et al., "On the development of a novel adaptive prosthetic hand with compliant joints: experimental platform and EMG control", IEEE/RSJ International Conference on Intelligence Robots and Systems (Edmonton, Aug. 2-6, 2005), 2005 (Date added to IEEE Xplore: Dec. 2005), pp. 1271-1276 <DOI:10.1109/IROS.2005.1545585>.

Kearney, R. et al., "Identification of nonlinearities in the neuromuscular system", Proceedings of IEEE Engineering in Medicine and Biology Society (New Orleans, LA, Nov. 4-7, 1988), 1988 (date added to IEEE Xplore: Apr. 2006), pp. 639-640 <DOI:10.1109/IEMBS.1988.94815>.

Keenan, K. et al., "Amplitude cancellation reduces the size of motor unit potentials averaged from the surface EMG", Journal of Applied Physiology, Jun. 2006, vol. 100, No. 6, pp. 1928-1937 <DOI:10.1152/japplphysiol.01282.2005>.

Keenan, K. et al., "Influence of amplitude cancellation on the simulated surface electromyogram", Journal of Applied Physiology, Jan. 2005, vol. 98, No. 1, pp. 120-131 <DOI:10.1152/japplphysiol.00894.2004>.

Kellis, S. et al., "Sensing millimeter-scale dynamics in cortical surface potentials for neural prosthetics", IEEE Sensors (Limerick, Ireland, Oct. 28-31, 2011), 2011 (date added to IEEE Xplore: Jan. 2012), pp. 1823-1826 <DOI:10.1109/ICSENS.2011.6127165>.

Kendell, C. et al., "A novel approach to surface electromyography: an exploratory study of electrode-pair selection based on signal characteristics", Journal of NeuroEngineering and Rehabilitation, Apr. 2012, vol. 9, No. 24, 8 pp. <DOI:10.1186/1743-0003-9-24>.

Khokhar, Z. et al., "Surface EMG pattern recognition for real-time control of a wrist exoskeleton", BioMedical Engineering OnLine, Aug. 2010, vol. 9, No. 41, 17 pp. <DOI:10.1186/1475-925X-9-41>.

Khushaba, R. et al., "Orthogonal Fuzzy Neighborhood Discriminant Analysis for Multifunction Myoelectric Hand Control", IEEE Trans-

(56) References Cited

OTHER PUBLICATIONS actions on Biomedical Engineering, Jun. 2010 (date of publication: Feb. 2010), vol. 57, No. 6, pp. 1410-1419 <DOI:10.1109/TBME.2009.2039480>.
Khushaba, R. et al., "Towards limb position invariant myoelectric pattern recognition using time-dependent spectral features", Neural Networks, Jul. 2014 (available online Mar. 2014), vol. 55, pp. 42-58 <DOI:10.1016/j.neunet.2014.03.010>.
Khushaba, R., "Correlation Analysis of Electromyogram Signals for Multiuser Myoelectric Interfaces", IEEE Transactions on Neural Systems and Rehabilitation Engineering, Jul. 2014 (date of publication: Feb. 2014), vol. 22, No. 4, pp. 745-755 <DOI:10.1109/TNSRE.2014.2304470>.
Kiguchi, K. et al., "Muscle-model-oriented EMG-based control of an upper-limb power-assist exoskeleton with a neuro-fuzzy modifier", IEEE International Conference on Fuzzy Systems (Hong Kong, China, Jun. 1-6, 2008), 2008 (date added to IEEE Xplore: Sep. 2008), pp. 1179-1184 <DOI:10.1109/FUZZY.2008.4630520>.
Kiso, A. et al., "Optimal mapping of torus self-organizing map for forearm motion discrimination based on EMG", Proceedings of SICE Annual Conference (Taipei, Taiwan, Aug. 18-21, 2010), 2010 (date added to IEEE Xplore: Oct. 2010), pp. 80-83.
Konrad, P., "The ABC of EMG: A Practical Introduction to Kinesiological Electromyography", Noraxon Inc., Mar. 2006, Version 1.4, pp. 1-60.
Krishnamoorthy, V. et al., "Muscle synergies during shifts of the center of pressure by standing persons: identification of muscle modes", Biological Cybernetics, Aug. 2003 (available online Jun. 2003), vol. 89, No. 2, pp. 152-161 <DOI:10.1007/s00422-003-0419-5>.
Kronander, K. et al., "Learning Compliant Manipulation through Kinesthetic and Tactile Human-Robot Interaction", IEEE Transactions on Haptics, Jul.-Sep. 2014 (date of publication: Oct. 2013), vol. 7, No. 3, pp. 367-380 <DOI:10.1109/TOH.2013.54>.
Krysztoforski, K. et al., "Recognition of Palm Finger Movements on the Basis of EMG Signals witht ehh Application of Wavelets", Task Quarterly, 2004, vol. 8, No. 2, pp. 269-280.
Kuiken, T. et al., "Targeted Muscle Reinnervation for Real-time Myoelectric Control of Multifunction Artificial Arms", Feb. 2009, vol. 301, No. 6, pp. 619-628 <DOI:10.1001/jama.2009.116>.
Kumar, P. et al., "An adaptive multi sensor data fusion with hybrid nonlinear ARX and Wiener-Hammerstein models for skeletal muscle force estimation", ICS Proceedings of the 14th WSEAS International Conference on Systems (Corfu, Greece, Jul. 22-24, 2010), 2010, vol. 1, pp. 186-191.
Kutch, J. et al., "Challenges and New Approaches to Proving the Existence of Muscle Synergies of Neural Origin", PLoS Computational Biology, May 2012, vol. 8, No. 5, article e1002434 <DOI:10.1371/journal.pcbi.1002434>.
Kutch, J. et al., "Endpoint Force Fluctuations Reveal Flexible Rather Than Synergistic Patterns of Muscle Cooperation", Journal of Neurophysiology, Nov. 2008, vol. 100, No. 5, pp. 2455-2471 <DOI:10.1152/jn.90274.2008>.
Lalitharatne, T. et al., "Towards Hybrid EEG-EMG-Based Control Approaches to be Used in Bio-robotics Applications: Current Status, Challenges and Future Directions", Paladyn, Journal of Behavioral Robotics, Dec. 2013, vol. 4, No. 2, pp. 147-154 <DOI:10.2478/pjbr-2013-0009>.
Lee, D. et al., "Algorithms for Non-negative Matrix Factorization", Advances in Neural Information Processing Systems '13 (Boston, MA), MIT Press, 2001, pp. 556-562.
Lee, W., "Neuromotor Synergies as a Basis for Coordinated Intentional Action", Journal of Motor Behavior, Jul. 1984 (available online Aug. 2013), vol. 16, No. 2, pp. 135-170 <DOI:10.1080/00222895.1984.10735316>.
Li, G. et al., "Quantifying Pattern Recognition-Based Myoelectric Control of Multifunctional Transradial Prostheses", IEEE Transactions on Neural Systems and Rehabilitation Engineering, Apr. 2010 (date of publication: Jan. 2010), vol. 18, No. 2, pp. 185-192 <DOI:10.1109/TNSRE.2009.2039619>.
Li, Y. et al., "Automatic recognition of sign language subwords based on portable accelerometer and EMG sensors", International Conference on Multimodal Interfaces and the Workship on Machine Learning of Multimodal Interaction (Beijing, China, Nov. 8-10, 2010), 2010, article 17, 7 pages <DOI:10.1145/1891903.1891926>.
Liarokapis, M. et al., "Learning human reach-to-grasp strategies: Towards EMG-based control of robotic arm-hand systems", IEEE International Conference on Robotics and Automation (St. Paul, MN, May 14-18, 2012), 2012 (date added to IEEE Xplore: Jun. 2012), pp. 2287-2292 <DOI:10.1109/ICRA.2012.6225047>.
Linda, O. et al., "Fuzzy Force-Feedback Augmentation for Manual Control of Multirobot System", IEEE Transactions on Industrial Electronics, Aug. 2011 (date of publication: Aug. 2010), vol. 58, No. 8, pp. 3213-3220 <DOI:10.1109/TIE.2010.2068532>.
Liu, H. et al., "Multi-class surface EMG classification using support vector machines and wavelet transform", 2010 8th World Congress on Intelligent Control and Automation (Jinan, China, Jul. 7-9, 2010), 2010 (date added to IEEE Xplore: Aug. 2010), pp. 2963-2967 <DOI:10.1109/WCICA.2010.5554144>.
Liu, J. et al., "Reduced Daily Recalibration of Myoelectric Prosthesis Classifiers Based on Domain Adaptation", IEEE Journal of Biomedical and Health Informatics, Jan. 2016 (date of publication: Dec. 2014), vol. 20, No. 1, pp. 166-176 <DOI:10.1109/JBHI.2014.2380454>.
Liu, X. et al., "Contributions of Online Visual Feedback to the Learning and Generalization of Novel Finger Coordination Patterns", Journal of Neurophysiology, May 2008, vol. 99, No. 5, pp. 2546-2557 <DOI:10.1152/jn.01044.2007>.
Liu, X. et al., "Reorganization of Finger Coordination Patterns During Adaptation to Rotation and Scaling of a Newly Learned Sensorimotor Transformation", Journal of Neurophysiology, Jan. 2011, vol. 105, No. 1, pp. 454-473 <DOI:10.1152/jn.00247.2010>.
Lloyd, D. et al., "An EMG-driven musculoskeletal model to estimate muscle forces and knee joint moments in vivo", Journal of Biomechanics, Jun. 2003 (available online Mar. 2003), vol. 36, No. 6, pp. 765-776 <DOI:10.1016/S0021-9290(03)00010-1>.
Lock, B. et al., "Real-Time Myoelectric Control in a Virtual Environment to Relate Usability vs. Accuracy", Proceedings of the 2005 MyoElectric Controls/Powered Prosthetics Symposium (New Brunswick, Canada, Aug. 17-19, 2005), 2005, 4 pages.
Lorrain, T. et al., "Influence of the training set on the accuracy of surface EMG classification in dynamic contractions for the control of multifunction prostheses", Journal of NeuroEngineering and Rehabilitation, May 2011, vol. 8, No. 25, 8 pages <DOI:10.1186/1743-0003-8-25>.
Lovely, D. et al., "A computer-aided myoelectric training system for young upper limb amputees", Journal of Microcomputer Applications, Jul. 1990 (available online Nov. 2004), vol. 13, No. 3, pp. 245-259 <DOI:10.1016/0745-7138(90)90026-4>.
Lucas, M-F. et al., "Multi-channel surface EMG classification using support vector machines and signal-based wavelet optimization", Biomedical Signal Processing and Control, Apr. 2008 (available online Nov. 2007), vol. 3, No. 2, pp. 169-174 <DOI:10.1016/j.bspc.2007.09.002>.
Luchins, A., "Mechanization in problem solving: the effect of Einstellung", Psychological Monographs, 1942, vol. 54, No. 6, pp. i-95 <DOI:10.1037/h0093502>.
Lyman, J. et al., "Fundamental and applied research related to the design and development of upper-limb externally powered prostheses", Bulletin of Prosthetics Research, 1976, vol. 13, pp. 184-195.
Ma, S. et al., "EMG Biofeedback Based VR System for Hand Rotation and Grasping Rehabilitation", 14th International Conference Information Visualisation (London, UK, Jul. 26-29, 2010), 2010 (date added to IEEE Xplore: Sep. 2010), pp. 479-484 <DOI:10.1109/IV.2010.73>.
Gopura, R. et al., "A human forearm and wrist motion assist exoskeleton robot with EMG-based Fuzzy-neuro control", 2nd IEEE RAS & EMBS International Conference on Biomedical Robotics and Biomechatronics (Scottsdale, AZ, Oct. 19-22, 2008), 2008 (date added to IEEE Xplore Jan. 2009), pp. 550-555 <DOI:10.1109/BIOROB.2008.4762793>.
Graupe, D. et al., "Functional Separation of EMG Signals via ARMA Identification Methods for Prosthesis Control Purposes",

(56) References Cited

OTHER PUBLICATIONS

IEEE Transactions on Systems, Man, and Cybernetics, Mar. 1975, vol. SMC-5, No. 2, pp. 252-259 <DOI:10.1109/TSMC.1975.5408479>.

Ha, K. et al., "Volitional Control of a Prosthetic Knee Using Surface Electromyography", IEEE Transactions on Biomedical Engineering, Jan. 2011 (date of publication Aug. 2010), vol. 58, No. 1, pp. 144-151 <DOI:10.1109/TBME.2010.2070840>.

Hahne, J. et al., "Linear and Nonlinear Regression Techniques for Simultaneous and Proportional Myoelectric Control", IEEE Transactions on Neural Systems and Rehabilitation Engineering, Mar. 2014 (date of publication: Feb. 2014), vol. 22, No. 2, pp. 269-279 <DOI:10.1109/TNSRE.2014.2305520>.

Hahne, J. et al., "Simultaneous and proportional control of 2D wrist movements with myoelectric signals", IEEE International Workshop on Machine Learning for Signal Processing (Santander, Spain, Sep. 23-26, 2012), 2012 (date added to IEEE Xplore: Nov. 2012), 6 pages <DOI:10.1109/MLSP.2012.6349712>.

Hanley, J. et al., "The meaning and use of the area under a receiver operating characteristic (ROC) curve", Radiology, Apr. 1982, vol. 143, No. 1, pp. 29-36 <DOI:10.1148/radiology.143.1.7063747>.

Hargrove, L. et al., "A Comparison of Surface and Intramuscular Myoelectric Signal Classification", IEEE Transactions on Biomedical Engineering, May 2007 (date of publication: Apr. 2007), vol. 54, No. 5, pp. 847-853 <DOI:10.1109/TBME.2006.889192>.

Hargrove, L. et al., "Multiple Binary Classifications via Linear Discriminant Analysis for Improved Controllability of a Powered Prosthesis", IEEE Transactions on Neural Systems and Rehabilitation Engineering, Feb. 2010 (date of publication: Jan. 2010), vol. 18, No. 1, pp. 49-57 <DOI:10.1109/TNSRE.2009.2039590>.

Hargrove, L. et al., "Pattern recognition control outperforms conventional myoelectric control in upper limb patients with targeted muscle reinnervation", 35th Annual International Conference of the IEEE Engineering in Medicine and Biology Society (Osaka, Japan, Jul. 3-7, 2013), 2013 (Date added to IEEE Xplore: Sep. 2013), pp. 1599-1602 <DOI:10.1109/EMBC.2013.6609821>.

Hargrove, L. et al., "Principal Components Analysis Preprocessing for Improved Classification Accuracies in Pattern-Recognition-Based Myoelectric Control", IEEE Transactions on Biomedical Engineering, May 2009 (date of publication: Oct. 2008), vol. 56, No. 5, pp. 1407-1414 <DOI:10.1109/TBME.2008.2008171>.

Hargrove, L. et al., "The Effect of ECG Interference on Pattern-Recognition-Based Myoelectric Control for Targeted Muscle Reinnervated Patients", IEEE Transactions on Biomedical Engineering, Sep. 2009 (date of publication: Dec. 2008), vol. 56, No. 9, pp. 2197-2201 <DOI:10.1109/TBME.2008.2010392>.

Hargrove, L. et al., "The effect of electrode displacements on pattern recognition based myoelectric control", IEEE Engineering in Medicine and Biology Society (New York, NY, Aug. 30-Sep. 3, 2006), 2006 (date added to IEEE Xplore: Dec. 2016), pp. 2203-2206 <DOI:10.1109/IEMBS.2006.260681>.

Hart, C. et al., "Modular Premotor Drives and Unit Bursts as Primitives for Frog Motor Behaviors", Journal of Neuroscience, Jun. 2004, vol. 24, No. 22, pp. 5269-5282 <DOI:10.1523/JNEUROSCI.5626-03.2004>.

Heliot, R. et al., "Learning in Closed-Loop Brain-Machine Interfaces: Modeling and Experimental Validation", IEEE Transactions on Systems, Man, and Cybernetics, Part B, Oct. 2010 (date of publication: Dec. 2009), vol. 40, No. 5, pp. 1387-1397 <DOI:10.1109/TSMBC.2009.2036931>.

Hocaoglu, E. et al., "Tele-impedance control of a variable stiffness prosthetic hand", IEEE International Conference on Robotics and Biomimetrics (Guangzhou, China, Dec. 11-14, 2012), 2012 (date added to IEEE Xplore: Apr. 2013), pp. 1576-1582 <DOIO:10.1109/ROB10.2012.6491192>.

Hogan, N. et al., "Myoelectric Signal Processing: Optimal Estimation Applied to Electromyography—Part 1: Derivation of the Optimal Myoprocessor", IEEE Transactions on Biomedical Engineering, Jul. 1980, vol. BME-27, No. 7, pp. 382-395 <DOI:10.1109/TBME.1980.326652>.

Hogan, N., "Impedance Control: An Approach to Manipulation", American Control Conference (San Diego, CA, Jun. 6-8, 1984), 1984 (date added to IEEE Xplore: Mar. 2009), pp. 304-313 <DOI:10.23919/ACC.1984.4788393>.

Hogan, N., "Impedance Control: An Approach to Manipulation: Part 11-Implementation", Journal of Dynamic Systems, Measurement, and Control, Mar. 1985 (published online: Jul. 2009), vol. 107, No. 1, pp. 8-16 <DOI:10.1115/1.3140713>.

Hu, X. et al., "Classification of Surface EMG Signal Based on Energy Spectra Change", International Conference on BioMedical Engineering and Informatics (Sanya, China, May 27-30, 2008), 2008 (date added to IEEE Xplore: Jun. 2008), pp. 375-379 <DOI:10.1109/BMEI.2008.24>.

Hu, X. et al., "Feature Extraction of Surface EMG Signal Based on Wavelet Coefficient Entropy", 2nd International Conference on Bioinformatics and Biomedical Engineering (Shanghai, China, May 16-18, 2008), 2008 (date added to IEEE Xplore: Jun. 2008), pp. 1758-1760 <DOI:10.1109/ICBBE.2008.768>.

Hu, X. et al., "Multivariate AR modeling of electromyography for the classification of upper arm movements", Clinical Neurophysiology, Jun. 2004 (available online Feb. 2004), vol. 115, No. 6, pp. 1276-1287 <DOI:10.1016/j.clinph.2003.12.030>.

Huang, G. et al., "Spatio-spectral filters for low-density surface electromyographic signal classification", Medical & Biological Engineering & Computing, May 2013 (available online Feb. 2013), vol. 51, No. 5, pp. 547-555 <DOI:10.1007/s11517-012-1024-3>.

Huang, Y. et al., "A Gaussian mixture model based classification scheme for myoelectric control of powered upper limb prostheses", IEEE Transactions on Biomedical Engineering, Nov. 2005 (available online Oct. 2005), vol. 52, No. 11, pp. 1801-1811 <DOI:10.1109/TBME.2005.856295>.

Hudgins, B. et al., "A new strategy for multifunction myoelectric control", IEEE Transactions on Biomedical Engineering, Jan. 1993, vol. 40, No. 1, pp. 82-94 <DOI:10.1109/10.204774>.

Hug, F., "Can muscle coordination be precisely studied by surface electromyography?", Journal of Electromyography and Kinesiology, Feb. 2011 (available online Sep. 2010), vol. 21, No. 1, pp. 1-12 <DOI:10.1016/j.jelekin.2010.08.009>.

Hussein, S. et al., "Intention detection using a neuro-fuzzy EMG classifier", IEEE Engineering in Medicine and Biology Magazine, Nov.-Dec. 2002, vol. 21, No. 6, pp. 123-129 <DOI:10.1109/MEMB.2002.1175148>.

Ison, M. et al., "Beyond User-Specificity for EMG Decoding Using Multiresolution Muscle Synergy Analysis", ASME 2013 Dynamic Systems and Control Conference (Palo Alto, CA, Oct. 21-23, 2013), 2013, 6 page <DOI:10.1115/DSCC2013-4070>.

Ison, M. et al., "Enhancing Practical Multifunctional Myoelectric Applications through Implicit Motor Control Training Systems", 36th Annual International Conference of the IEEE Engineering in Medicine and Biology Society (Chicago, IL, Aug. 26-30, 2014), 2014 (date added to IEEE Xplore: Nov. 2014), pp. 3525-3528 <DOI:10.1109/EMBC.2014.6944383>.

Ison, M. et al., "High-Density Electromyography and Motor Skill Learning for Robust Long-TermControl of a 7-DoF Robot Arm", IEEE Transactions on Neural Systems and Rehabilitation Engineering, Apr. 2016 (date of publication: Mar. 2015), vol. 24, No. 4, pp. 424-433 <DOI:10.1109/TNSRE.2015.2417775>.

Ison, M. et al., "Learning efficient control of robots using myoelectric interfaces", IEEE International Conference on Robotics and Automation (Hong Kong, China, May 31-Jun. 7, 2014), 2014 (date added to IEEE Xplore: Sep. 2014), pp. 2880-2885 <DOI:10.1109/ICRA.2014.6907273>.

Ison, M. et al., "Multi-Directional Impedance Control with Electromyography for Compliant Human-Robot Interaction", IEEE International Conference on Rehabilitation Robotics (Singapore, Singapore, Aug. 11-14, 2015), 2015 (Date added to IEEE Xplore: Oct. 2015), pp. 416-421 <DOI:10.1109/ICORR.2015.7281235>.

Ison, M. et al., "Proportional Myoelectric Control of Robots: Muscle Synergy Development Drives Performance Enhancement, Retainment, and Generalization", IEEE Transactions on Robotics, Apr. 2015 (date of publication: Mar. 2015), vol. 31, No. 2, pp. 259-268 <DOI:10.1109/TRO.2015.2395731>.

(56) References Cited

OTHER PUBLICATIONS

Ison, M. et al., "Simultaneous myoelectric control of a robot arm using muscle synergy-inspired inputs from high-density electrode grids", IEEE International Conference on Robotics and Automation (Seattle, WA, May 26-30, 2015), 2015 (date added to IEEE Xplore: Jul. 2015), pp. 6469-6474 <DOI:10.1109/ICRA.2015.7140108>.

Ison, M. et al., "The role of muscle synergies in myoelectric control: trends and challenges for simultaneous multifunction control", Journal of Neural Engineering, Sep. 2014, vol. 11, No. 5, article 051001, 22 pages <DOI:10.1088/1741-2560/11/5/051001>.

Ivanenko, Y. et al., "Coordination of Locomotion with Voluntary Movements in Humans", Journal of Neuroscience, Aug. 2005, vol. 25, No. 31, pp. 7238-7253 <DOI:10.1523/JNEUROSCI.1327-05.2005>.

Ivanenko, Y. et al., "Motor Control Programs and Walking", The Neuroscientist, Aug. 2006, vol. 12, No. 4, pp. 339-348. <DOI:10.1177/1073858406287987>.

Jesunathadas, M. et al., "Influence of amplitude cancellation on the accuracy of determining the onset of muscle activity from the surface electromyogram", Journal of Electromyography and Kinesiology, Jun. 2012, vol. 22, No. 3, pp. 494-500 <DOI:10.1016/j.jelekin.2012.01.011>.

Jiang, A. et al., "Adaptive grip control on an uncertain object", IEEE/RSJ International Conference on Intelligent Robots and Systems (Vilamoura, Portugal, Oct. 7-12, 2012), 2012 (date added to IEEE Xplore: Dec. 2012), pp. 1161-1166 <DOI:10.1109/IROS.2012.6385922>.

Jiang, N. et al., "EMG-based simultaneous and proportional estimation of wrist/hand kinematics in uni-lateral trans-radial amputees", Journal of NeuroEngineering and Rehabilitation, Jun. 2012, vol. 9, No. 42, 11 pages <DOI:10.1186/1743-0003-9-42>.

Jiang, N. et al., "Extracting Simultaneous and Proportional Neural Control Information for Multiple-DOF Prostheses From the Surface Electromyographic Signal", IEEE Transactions on Biomedical Engineering, Apr. 2009 (date of publication: Oct. 2008), vol. 56, No. 4, pp. 1070-1080 <DOI:10.1109/TBME.2008.2007967>.

Jiang, N. et al., "Intuitive, Online, Simultaneous, and Proportional Myoelectric Control Over Two Degrees-of-Freedom in Upper Limb Amputees", IEEE Transactions on Neural Systems and Rehabilitation Engineering, May 2014 (date of publication: Aug. 2013), vol. 22, No. 3, pp. 501-510 <DOI:10.1109/TNSRE.2013.2278411>.

Jiang, N. et al., "Is Accurate Mapping of EMG Signals on Kinematics Needed for Precise Online Myoelectric Control?", IEEE Transactions on Neural Systems and Rehabilitation Engineering, May 2014 (date of publication: Oct. 2013), vol. 22, No. 3, pp. 549-558 <DOI:10.1109/TNSRE.2013.2287383>.

Jiang, N. et al., "Myoelectric Control of Artificial Limbs-Is There a Need to Change Focus? [In the Spotlight]", IEEE Signal Processing Magazine, Sep. 2012 (date of publication: Aug. 2012), vol. 29, No. 5, 4 pp. <DOI:10.1109/MSP.2012.2203480>.

Kadiallah, A. et al., "Impedance control is selectively tuned to multiple directions of movement", Journal of Neurophysiology, Nov. 2011 (available online Aug. 2011), vol. 106, No. 5, pp. 2737-2748 <DOI:10.1152/jn.00079.2011>.

Kamavuako, E. et al., "Combined surface and intramuscular EMG for improved real-time myoelectric control performance", Biomedical Signal Processing and Control, Mar. 2014 (available online Feb. 2014), vol. 10, pp. 102-107 <DOI:10.1016/j.bspc.2014.01.007>.

Kargo, W. et al., "Early Skill Learning Is Expressed through Selection and Tuning of Cortically Represented Muscle Synergies", Journal of Neuroscience, Dec. 2003, vol. 23, No. 35, pp. 11255-11269 <DOI:10.1523/JNEUROSCI.23-35-11255.2003>.

Karlik, B. et al., "A fuzzy clustering neural network architecture for multifunction upper-limb prosthesis", IEEE Transactions on Biomedical Engineering, Nov. 2003 (date of publication: Oct. 2003), vol. 50, No. 11, pp. 1255-1261 <DOI:10.1109/TBME.2003.818469>.

Karlsson, S. et al., "Time-frequency analysis of myoelectric signals during dynamic contractions: a comparative study", IEEE Transactions on Biomedical Engineering, Feb. 2000, vol. 47, No. 2, pp. 228-238 <DOI:10.1109/10.821766>.

Kato, R. et al., "Real-time Learning Method for Adaptable Motion-Discrimination using Surface EMG Signal", IEEE/RSJ International Conference on Intelligent Robots and Systems (Beijing, China, Oct. 9-15, 2006), 2006 (date added to IEEE Xplore: Jan. 2007), pp. 2127-2132 <DOI:10.1109/IROS.2006.282492>.

Kawai, S. et al., "Study for control of a power assist device. Development of an EMG based controller considering a human model", IEEE/RSJ International Conference on Intelligent Robots and Systems (Sendai, Japan, Sep. 28-Oct. 2, 2004), 2004 (date added to IEEE Xplore: Feb. 2005), pp. 2283-2288 <DOI:10.1109/IROS.2004.1389749>.

Abbasi-Asl, R., R. Khorsandi, S. Farzampour and E. Zahedi, "Estimation of Muscle Force with EMG Signals Using Hammerstein-Wiener Model", in "5th Kuala Lumpur International Conference on Biomedical Engineering 2011", pp. 157-160 (Springer, 2011).

Mizuno, H. et al., "Forearm motion discrimination technique using real-time EMG signals", Annual International Conference of the IEEE Engineering in Medicine and Biology Society (Boston, MA, Aug. 30-Sep. 3, 2011), 2011 (date added to IEEE Xplore: Dec. 2011), pp. 4435-4438 <DOI:10.1109/IEMBS.2011.6091100>.

Moon, I. et al., "Wearable EMG-based HCI for Electric-Powered Wheelchair Users with Motor Disabilities", Proceedings of the 2005 IEEE International Conference on Robotics and Automation (Barcelona, Spain, Apr. 18-22, 2005), 2005 (date added to IEEE Xplore: Jan. 2006), pp. 2649-2654 <DOI:10.1109/ROBOT.2005.1570513>.

Morin, E., "Identifying the EMG-force relationship", Proceedings of the 17th International Conference of the Engineering in Medicine and Biology Society (Montreal, Canada, Sep. 20-23, 1995), 1995 (date added to IEEE Xplore: Aug. 2002), pp. 1397-1398 <DOI:10.1109/IEMBS.1995.579745>.

Mosier, K. et al., "Remapping Hand Movements in a Novel Geometrical Environment", Journal of Neurophysiology, Jan. 2006, vol. 94, No. 6, pp. 4362-4372 <DOI:10.1152/jn.00380.2005>.

Moslem, B. et al., "Classification of multichannel uterine EMG signals by using unsupervised competitive learning", IEEE Workshop on Signal Processing Systems (Beirut, Lebanon, Oct. 4-7, 2011), 2011 (date added to IEEE Xplore: Dec. 2011), pp. 267-272 <DOI:10.1109/SiPS.2011.6088987>.

Muceli, S. et al., "Extracting Signals Robust to Electrode Number and Shift for Online Simultaneous and Proportional Myoelectric Control by Factorization Algorithms", IEEE Transactions on Neural Systems and Rehabilitation May 2014 (date of publication: Oct. 2013), vol. 22, No. 3, pp. 623-633 <DOI:10.1109/TNSRE.2013.2282898>.

Muceli, S. et al., "Identifying Representative Synergy Matrices for Describing Muscular Activation Patterns During Multidirectional Reaching in the Horizontal Plane", Journal of Neurophysiology, Mar. 2010, vol. 103, No. 3, pp. 1532-1542 <DOI:10.1152/jn.00559.2009>.

Muceli, S. et al., "Multichannel surface EMG based estimation of bilateral hand kinematics during movements at multiple degrees of freedom", Annual International Conference of the IEEE Engineering in Medicine and Biology Aires, Argentina, (Buenos Aug. 31-Sep. 4, 2010), 2010 (date added to IEEE Xplore: Nov. 2010), pp. 6066-6069 <DOI:10.1109/IEMBS.2010.5627622>.

Muceli, S. et al., "Simultaneous and Proportional Estimation of Hand Kinematics From Emg During Mirrored Movements at Multiple Degrees-of-Freedom", IEEE Transactions on Neural Systems and Rehabilitation Engineering, May 2012 (date of publication: Dec. 2011), vol. 20, No. 3, pp. 371-378 <DOI:10.1109/TNSRE.2011.2178039>.

Mussa-Ivaldi, F. et al., "Sensory motor remapping of space in human-machine interfaces", Progress in Brain Research, Jul. 2011, vol. 191, pp. 45-64 <DOI:10.1016/13978-0-444-53752-2.00014-X>.

Naik, G. et al., "Multi run ICA and surface EMG based signal processing system for recognising hand gestures", IEEE International Conference on Computer and Information Technology (Sydney, Australia, Jul. 8-11, 2008), 2008 (date added to IEEE Xplore: Aug. 2008), pp. 700-705 <DOI:10.1109/CIT.2008.4594760>.

(56) References Cited

OTHER PUBLICATIONS

Naik, G. et al., "Twin SVM for Gesture Classification Using the Surface Electromyogram", IEEE Transactions on Information Technology in Biomedicine, Mar. 2010 (date of publication: Dec. 2009), vol. 14, No. 2, pp. 301-308 <DOI:10.1109/TITB.2009.2037752>.

Nazarpour, K. et al., "Application of Higher Order Statistics to Surface Electromyogram Signal Classification", IEEE Transactions on Biomedical Engineering, Oct. 2007 (date of publication: Sep. 2007), vol. 54, No. 10, pp. 1762-1769 <DOI:10.1109/TBME.2007.894829>.

Nazarpour, K. et al., "Flexible Cortical Control of Task-Specific Muscle Synergies", Journal of Neuroscience, Sep. 2012, vol. 32, No. 36, pp. 12349-12360 <DOI:10.1523/JNEUROSCI.5481-11.2012>.

Nazarpour, K. et al., "Negentropy analysis of surface electromyogram signal", IEEE/SP 13th Workshop on Statistical Signal Processing (Bordeaux, France, Jul. 17-20, 2005), 2005 (date added to IEEE Xplore: May 2006), pp. 974-977 <DOI:10.1109/SSP.2005.1628736>.

Neptune, R. et al., "Modular control of human walking: A simulation study", Journal of Biomechanics, Jun. 2009 (available online Apr. 2009), vol. 42, No. 9, pp. 1282-1287 <DOI:10.1016/j.jbiomech.2009.03.009>.

Nielsen, J. et al., "Simultaneous and Proportional Force Estimation for Multifunction Myoelectric Prostheses Using Mirrored Bilateral Training", IEEE Transactions on Biomedical Engineering, Mar. 2011 (date of publication: Aug. 2010), vol. 58, No. 3, pp. 681-688 <DOI:10.1109/TBME.2010.2068298>.

Nilas, P. et al., "An innovative high-level human-robot interaction for disabled persons", IEEE International Conference on Robotics and Automation (New Orleans, LA, Apr. 26-May 1, 2004), 2004 (date added to IEEE Xplore: Jul. 2004), pp. 2309-2314 <DOI:10.1109/ROBOT.2004.1307406>.

Nishikawa, D. et al., "EMG prosthetic hand controller using real-time learning method", IEEE International Conference on Systems, Man, and Cybernetics (Tokyo, Japan, Oct. 12-15, 1999), 1999 (date added to IEEE Xplore: Aug. 2002), pp. 153-158 <DOI:10.1109/ICSMC.1999.814077>.

Norman, R. et al., "Electromechanical delay in skeletal muscle under normal movement conditions", Acta Physiologica, Jul. 1979 (available online: Dec. 2008), vol. 106, No. 3, pp. 241-248 <DOI:10.1111/j.1748-1716.1979.tb06394.x>.

Olree, K. et al., "Fundamental patterns of bilateral muscle activity in human locomotion", Biological Cybernetics, Oct. 1995, vol. 73, No. 5, pp. 409-414.

Oppenheim, H. et al., "WiiEMG: a real-time environment for control of the Wii with surface electromyography", Proceedings of IEEE International Symposium on Circuits and Systems (Paris, France, May 30-Jun. 2, 2010), 2010 (date added to IEEE Xplore: Aug. 2010), pp. 957-960 <DOI:10.1109/ISCAS.2010.5537390>.

Orabona, F. et al., "Model adaptation with least-squares SVM for adaptive hand prosthetics", IEEE International Conference on Robotics and Automation (Kobe, Japan, May 12-17, 2009), 2009 (date added to IEEE Xplore: Jul. 2009), pp. 2897-2903 <DOI:10.1109/ROBOT.2009.5152247>.

Orsborn, A. et al., "Creating new functional circuits for action via brain-machine interfaces", Frontiers in Computational Neuroscience, Nov. 2013, vol. 7, article 157, 10 pages <DOI:10.3389/fncom.2013.00157>.

Oskoei, M. et al., "Myoelectric control systems-A survey", Biomedical Signal Processing and Control, Oct. 2007 (available online Sep. 2007), vol. 2, No. 4, pp. 275-294 <DOI:10.1016/j.bspc.2007.07.009>.

Oskoei, M. et al., "Support Vector Machine-Based Classification Scheme for Myoelectric Control Applied to Upper Limb", IEEE Transactions on Biomedical Engineering, Aug. 2008 (date of publication: Mar. 2008), vol. 55, No. 8, pp. 1956-1965 <DOI:10.1109/TBME.2008.919734>.

Palla, S. et al., "Power spectral analysis of the surface electromyogram of human jaw muscles during fatigue", Archives of Oral Biology, 1981, vol. 26, No. 7, pp. 547-553 <DOI:10.1016/0003-9969(81)90016-9>.

Park, S-H. et al., "EMG pattern recognition based on artificial intelligence techniques", IEEE Transactions on Rehabilitation Engineering, Dec. 1998, vol. 6, No. 4, pp. 400-405 <DOI:10.1109/86.736154>.

Parker, P. et al., "Myoelectric signal processing for control of powered limb prostheses", Journal of Electromyography and Kinesiology, Dec. 2006 (available online Oct. 2006), vol. 16, No. 6, pp. 541-548 <DOI:10.1016/j.jelekin.2006.08.006>.

Patel, H. et al., "On the Effect of Muscular Cocontraction on the 3-D Human Arm Impedance", IEEE Transactions on Biomedical Engineering, Oct. 2014 (date of publication: May 2014), vol. 61, No. 10, pp. 2602-2608 <DOI:10.1109/TBBME.2014.2323938>.

Peerdeman, B. et al., "Myoelectric forearm prostheses: state of the art from a user-centered perspective", Journal of Rehabilitation Research and Development, 2011, vol. 48, No, 6, pp. 719-738.

Peleg, D. et al., "Classification of finger activation for use in a robotic prosthesis arm", IEEE Transactions on Neural Systems and Rehabilitation Engineering, Dec. 2002, vol. 10, No. 4, pp. 290-293 <DOI:10.1109/TNSRE.2002.806831>.

Peterlik, I. et al., "Constraint-Based Haptic Rendering of Multirate Compliant Mechanisms", IEEE Transactions on Haptics, Jul.-Sep. 2011 (date of publication: Jul. 2011), vol. 4, No. 3, pp. 175-187 <DOI:10.1109/TOH.2011.41>.

Pilarski, P. et al., "Online human training of a myoelectric prosthesis controller via actor-critic reinforcement learning", IEEE International Conference on Rehabilitation Robotics (Zurizh, Switzerland, Jun. 29-Jul. 1, 2011), 2011 (date added to IEEE Xplore: Aug. 2011), 7 pages <DOI:10.1109/ICORR.2011.5975338>.

Pistohl, T. et al., "Abstract and Proportional Myoelectric Control for Multi-Fingered Hand Prostheses", Annals of Biomedical Engineering, Dec. 2013 (available online: Aug. 2013), vol. 41, No. 12, pp. 2687-2698 <DOI:10.1007/s10439-013-0876-5>.

Powell, M. et al., "A Training Strategy for Learning Pattern Recognition Control for Myoelectric Prostheses", Journal of Prosthetics and Orthotics, Jan. 2013, vol. 25, No. 1, pp. 30-41 <DOI:10.1097/JP0.0b013e31827af7c1>.

Quigley, M. et al., "A low-cost compliant 7-DOF robotic manipulator", IEEE International Conference on Robotics and Automation (Shanghai, China, May 9-13, 2011), 2011 (date added to IEEE Xplore: Aug. 2011), pp. 6051-6058 <DOI:10.1109/ICRA.2011.5980332>.

Radhakrishnan, S. et al., "Learning a Novel Myoelectric-Controlled Interface Task", Journal of Neurophysiology, Oct. 2008, vol. 100, No. 4, pp. 2397-2408 <DOI:10.1152/jh.90614.2008>.

Rasmussen, C. et al., "Gaussian Processes for Machine Learning (GPML) Toolbox", Journal of Machine Learning Research, Nov. 2010, vol. 11, pp. 3011-3015.

Rau, G. et al., "Principles of high-spatial-resolution surface EMG (HSR-EMG): single motor unit detection and application in the diagnosis of neuromuscular disorders", Journal of Electromyography and Kinesiology, Dec. 1997 (available online Aug. 2001), vol. 7, No. 4, pp. 233-239 <DOI:10.1016/S1050-6411(97)00007-2>.

Reaz, M. et al., "Techniques of EMG signal analysis: detection, processing, classification and applications", Biological Procedures Online, Mar. 2006, vol. 8, pp. 11-35 <DOI:10.1251/bpo115>.

Rechy-Ramirez, E. et al., "Stages for Developing Control Systems using EMG and EEG Signals: a survey", University of Essex Technical Report: CES-513, Jun. 2011, 33 pages.

Roche, A. et al., "Prosthetic Myoelectric Control Strategies: A Clinical Perspective", Current Surgery Reports, Mar. 2014 (available online Jan. 2014), vol. 2, No. 44, 11 pages <DOI:10.1007/s40137-013-0044-8>.

Rojas-Martinez, M. et al., "Identification of isometric contractions based on High Density EMG maps", Journal of Electromyography and Kinesiology, Feb. 2013 (available online Jul. 2012), vol. 23, No. 1, pp. 33-42 <DOI:10.1016/j.jelekin.2012.06.009>.

Rosen, J. et al., "Performances of Hill-Type and Neural Network Muscle Models—Toward a Myosignal-Based Exoskeleton", Com-

(56) References Cited

OTHER PUBLICATIONS puters and Biomedical Research, Oct. 1999 (available online May 2002), vol. 32, No. 5, pp. 415-439 <DOI:10.1006/cbmr.1999.1524>.

Sahin, U. et al., "Pattern recognition with surface EMG signal based wavelet transformation", IEEE International Conference on Systems, Man and Cybernetics (Seol, South Korea, Oct. 14-17, 2012), 2012 (date added to IEEE Xplore: Dec. 2012), pp. 295-300 <DOI:10.1109/ICSMC.2012.6377717>.

Saltiel, P. et al., "Muscle Synergies Encoded Within the Spinal Cord: Evidence From Focal Intraspinal NMDA Iontophoresis in the Frog", Journal of Neurophysiology, Feb. 2001, vol. 85, No. 2, pp. 605-619 <DOI:10.1152/jn.2001.85.2.605>.

Sandford, T., "The $23.5 Billion Industry You'll Feel Good About Investing in" [online], Investment U, Jun. 2014 [retrieved Jun. 7, 2019 from investmentu.com], retrieved from the internet: <URL:https://www.investmentu.com/article/detail/38042/invest-prosthetic-technology#.XPogABZKhhE>.

Sanger, T., "Bayesian Filtering of Myoelectric Signals", Journal of Neurophysiology, Feb. 2007, vol. 97, No. 2, pp. 1839-1845 <DOI:10.1152/jn.00936.2006>.

Saponas, S. et al., "Demonstrating the Feasibility of Using Forearm Electromyography for Muscle-Computer Interfaces", CHI '08 Proceedings of the SIGCHI Conference on Human Factors in Computing Systems (Florence, Italy, Apr. 5-10, 2008), pp. 515-524.

\* cited by examiner

SYSTEMS AND METHODS FOR SIMULTANEOUS POSITION AND IMPEDANCE CONTROL FOR MYOELECTRIC INTERFACES

CROSS REFERENCE TO RELATED APPLICATIONS

This is a non-provisional application that claims benefit to U.S. provisional application Ser. No. 62/346,644, filed on Jun. 7, 2016, which is herein incorporated by reference in its entirety.

FIELD

The present disclosure generally relates to systems and methods for controlling a robot such as a prosthetic and in particular to systems and methods for simultaneous position and impedance control for myoelectric interfaces.

BACKGROUND

Compliant human-robot interaction is an essential component for integrating robots into everyday life. Many daily activities require variable impedance, and humans desire the same functionality when interacting with robots. Impedance control allows safe interaction with uncertain environments, enhancing both utility and viability. Surface electromyography (sEMG) has been identified as a candidate for naturally controlling variable impedance. During co-contraction, surface signals detected by sEMG correlate with the stiffness of corresponding joints. This correlation may be used in myoelectric impedance controllers. A neural network was trained to map the intensity of flexor and extensor forearm sEMG to the stiffness value of a prosthetic hand as it opened and closed, which in turn may be used to grip uncertain objects with the appropriate force. A similar impedance control, tele-impedance, may be applied to control a prosthetic hand aimed at generalizing grasping capabilities using kinematic synergies. The sEMG of quadriceps and hamstring muscles may be mapped to control stiffness and set-point angle for joint impedance of a prosthetic knee. There is thus a natural connection between sEMG and compliant controllers, with the controller designed to vary uniform stiffness of a prosthetic device based on sEMG.

Studies in neurophysiology indicate that humans not only control the intensity of their joint stiffness, but also the direction. While interacting in unstable environments, humans adapt their muscle activity to stabilize motion relative to the direction of instability. This suggests that multi-directional impedance control would provide a more natural extension to, and enhance capabilities of, human-robot interfaces. However, due to transient changes in sEMG, conventional myoelectric interfaces have struggled to provide reliable simultaneous control of motion, thereby deterring EMG-based impedance controllers from extending beyond a single degree-of-freedom (DOF).

BRIEF DESCRIPTION OF THE DRAWINGS

The patent or application file contains at least one drawing executed in color. Copies of this patent or patent application publication with color drawings will be provided by the Office upon request and payment of the necessary fee.

Corresponding reference characters indicate corresponding elements among the view of the drawings. The headings used in the figures do not limit the scope of the claims.

DETAILED DESCRIPTION

This disclosure presents a novel control scheme for the first time offering multi-directional impedance and position control in myoelectric interfaces. Recent works have shown that motor skill learning properties equally apply to myoelectric controls. Properties such as control refinement, retention, generalization, and transfer allow users to learn simultaneous and proportional motion simply by interacting with a myoelectric interface, regardless of its initial intuitiveness. The proposed scheme expands on these motor learning approaches by implementing a multidirectional impedance controller in this framework. Two definitions of stiffness are defined herein:

1) anisotropic: directional (non-uniform) stiffness, such that external forces produce a displacement magnitude dependent on the direction of the force.

2) isotropic: non-directional (uniform) stiffness, such that external forces produce a displacement magnitude independent of the direction of the force.

This technique demonstrates motor skill learning without requiring retraining between sessions. Using sEMG inputs from upper limb muscles, users simultaneously control both the stiffness and set-point of 3-DOFs. Users stabilize control in the presence of external forces in an analogous way to natural limb movements. Despite having no haptic feedback, subjects learn to tune the stiffness of the object being controlled to stabilize movement along desired paths.

II. Methods

A five-session experiment was designed for subjects to learn the multi-directional impedance control with a 3-DOF virtual myoelectric interface. Throughout each session, performance metrics verified the subjects were demonstrating characteristics of standard motor skill-type learning. Each subject learned the general controls while performing tasks without any external forces for three sessions on distinct days. Subjects returned for two additional sessions in which additional tasks were introduced requiring either anisotropic or isotropic impedance control. Finally, the method was demonstrated on a KUKA Light Weight Robot 4 (LWR 4) with a Touch Bionics iLIMB Ultra prosthetic hand while grasping objects and interacting with external forces.

A. Control Paradigm

Figure 1:
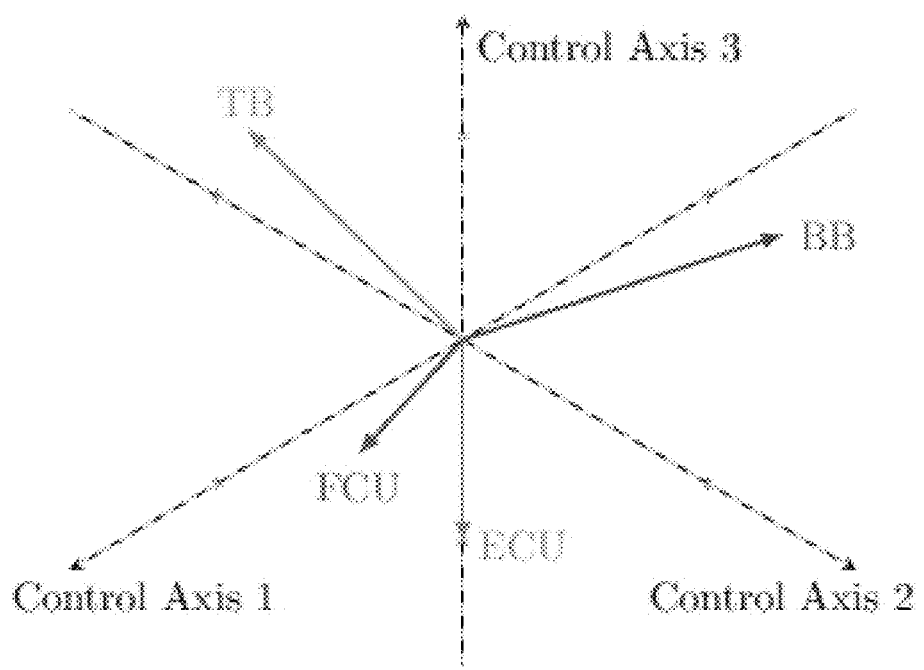
FIG. 1 is a graph showing a visualization of mapping W from sEMG e to output motions u.

The multi-directional impedance control algorithm is an extension of the velocity control method. i incoming sEMG signals, e, are linearly mapped to c output controls, u, after accounting for a muscle activity threshold a and output gain g:

$$u = gW[(e-o')ou(e-o')] \quad (1)$$

where o is an element-wise matrix multiplication, u(*) is the unit step function, and W is a (c×i) mapping function designed to map the entire output space using equal contributions from all inputs (FIG. 1).

Subjects have consistently shown a capacity to learn such a mapping function regardless of its intuitiveness. When c<i, the mapping is subjective, introducing control redundancies. That is, the magnitude of the output, |u|, is independent of the magnitude of the input, |e|, because some muscle contributions may cancel out the contributions of others with respect to the resulting motion.

Figure 2:
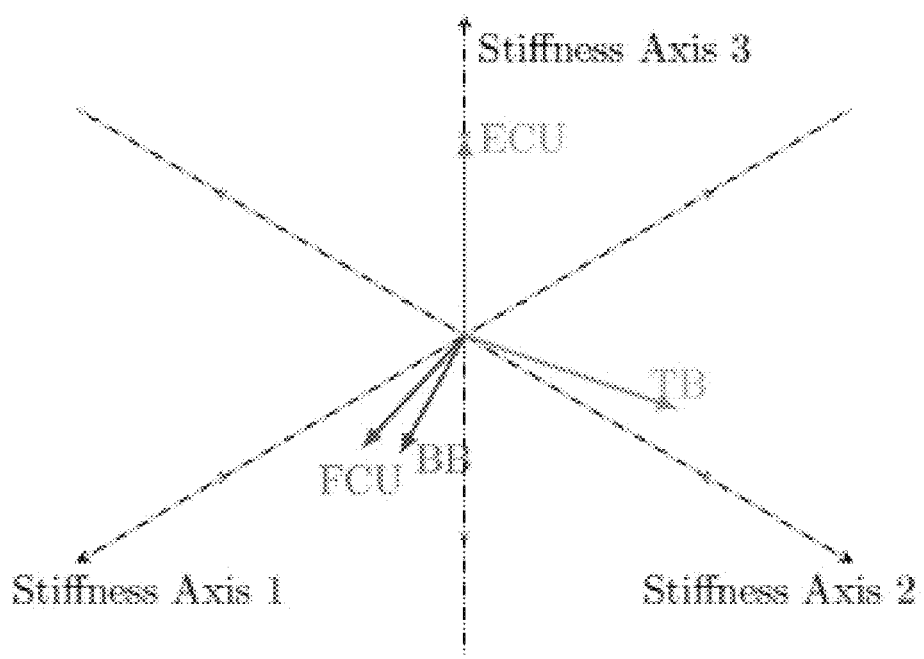
FIG. 2 is a graph showing a visualization of mapping S from sEMG e to output stiffness k.

The proposed multi-directional impedance control uses this redundancy to generate c directional stiffness outputs k with magnitudes proportional to |e|. Thus, $$k = gS|e-o'|ou(e-o')] \quad (2)$$

where S=abs(W) is the element-wise absolute value of matrix W (FIG. 2). This definition of k intuitively assigns stiffness directions for individual muscle contributions to the same axis as its corresponding motion. However, the overall stiffness direction is decoupled from motion outputs, as desired, despite both having the same input space. Thus, with anisotropic stiffness, the primary stiffness direction is not necessarily the primary motion direction. Similarly, isotropic stiffness can be achieved without requiring motion.

With both a motion and stiffness component, the impedance controller is adapted with $$a = ko[x-x_d] - bI^c v + f_{ext} \quad (3)$$

where x and v are the current position and velocity of the object, a is the resulting acceleration, $I^c$ is the c×c identity matrix, b is a scalar (isotropic damping term, $f_{ext}$ is external force, and $x_d$ is the commanded set point:

$$x_d = x + u\Delta t \quad (4)$$

where $\Delta t$ is the sampling rate. Inertia tensors are ignored in the virtual interface.

In this experiment, EMG inputs from four muscles (i=4)—Biceps Brachii (BB), Triceps Brachii (TB), Flexor Carpi Ulnaris (FCU), and Extensor Carpi Ulnaris (ECU)—are mapped to three control outputs (c=3)—x, y, and z (virtual)/hand motion (robot)—and W is arbitrarily chosen following the three criteria specified in (FIG. 1):

$$M = \begin{bmatrix} -0.79 & -0.06 & 0.85 & 0.00 \\ -0.52 & 0.94 & -0.42 & 0.00 \\ 0.33 & 0.34 & 0.33 & -1.00 \end{bmatrix} \quad (5)$$

The corresponding S is then (see FIG. 2):

$$S = \begin{bmatrix} 0.79 & 0.06 & 0.85 & 0.00 \\ 0.52 & 0.94 & 0.42 & 0.00 \\ 0.33 & 0.34 & 0.33 & 1.00 \end{bmatrix} \quad (6)$$

1) EMG Processing: The raw sEMG signals of four upper arm muscles are collected, rectified, low-pass filtered (fourth-order zero-lag Butterworth, cut-off 3 Hz), and normalized with respect to the subject's maximal voluntary contraction (MVC) to generate e. These signals are then subsampled to $$\frac{1}{\Delta t} = 200 \text{ Hz}$$

for input to (4). To simulate continuous control, (3) is computed at f=2000 Hz. For stability, b=2f, and all elements of k were scaled between $$0 \text{ and } \frac{b^2}{4};$$

based on MVC values. This ensures the system is both stable and critically damped at its highest stiffness.

Before each session, subjects perform their MVC for each muscle to scale sEMG and set external force magnitudes during isotropic and anisotropic tasks.

2) Robot Control: LWR 4 operates in Cartesian impedance control, effectively replacing (3) with its internal system and actual external forces. During this session, (2) and (4) were updated at 200 Hz according to the specifications of the robot. In contrast, only velocity commands can be sent to the iLIMB, so all compliance interaction was reserved for LWR 4. Velocity commands were sent via a wired connection and/or a wireless connection (e.g., Bluetooth) to the iLIMB for the purpose of opening and closing all fingers, in correspondence with Control Axis 3, also at 200 Hz.

B. Experimental Setup

Figure 3:
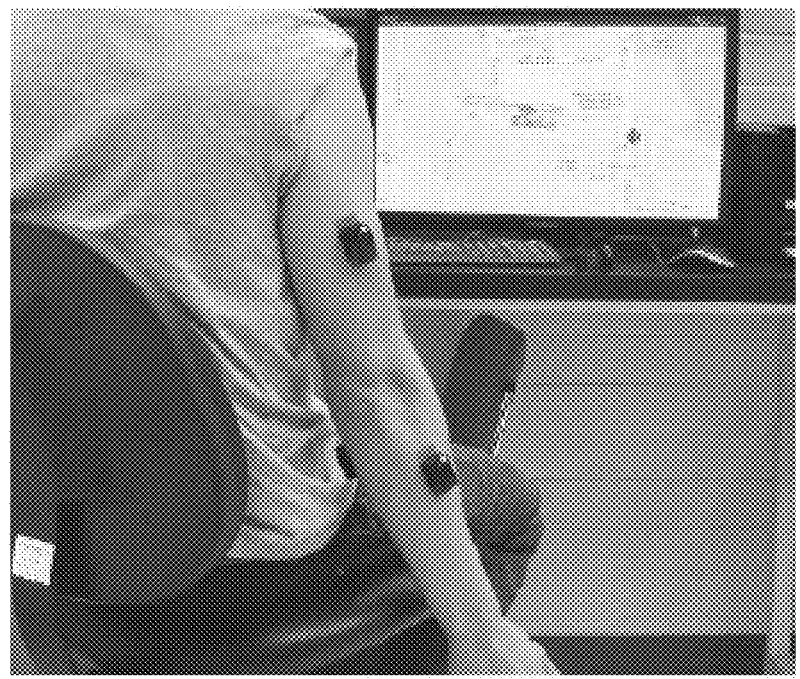
FIG. 3 is a picture showing the Virtual Reality (VR) control setup including the sEMG system and monitor.

Four wireless sEMG electrodes (Delsys Trigno Wireless) were acquired from the BB, TB, FCU, and ECU with a gain of 500, digitized with 16-bit depth at a frequency of 1926 Hz and broadcast via TCP. Both the virtual reality (VR) and robot interfaces receive commands at 200 Hz from a custom program using C++ and OpenGL API. The setup for interacting with both the VR and robot are shown in FIGS. 3 and 10, respectively.

C. Experimental Protocol

Subjects, unaware how to control the interface, attended five sessions across a span of two weeks.

Figure 4A:
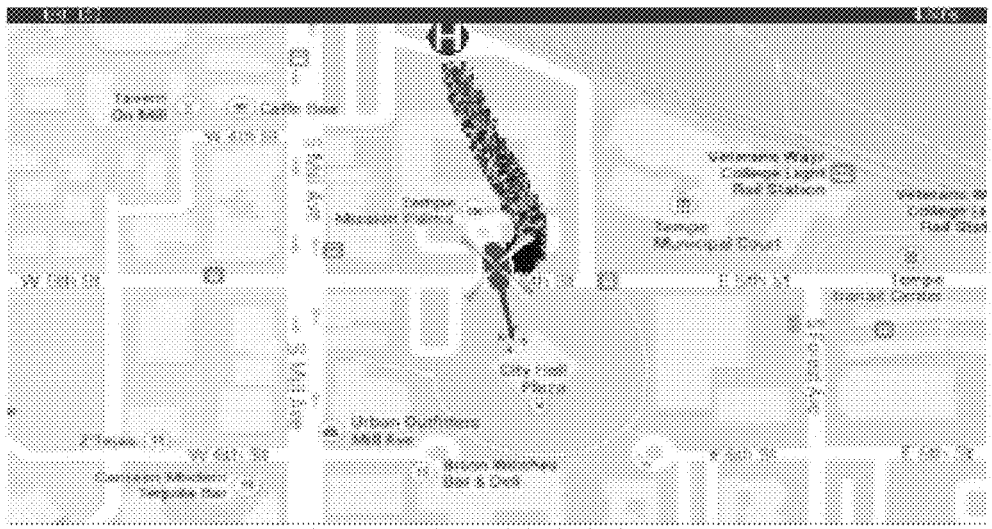
FIG. 4A is an illustration showing the normal control task with no external forces for controlling a virtual helicopter by a subject and FIG. 4B is an illustration showing an anisotropic task for controlling a virtual helicopter by a subject.
Figure 4B:
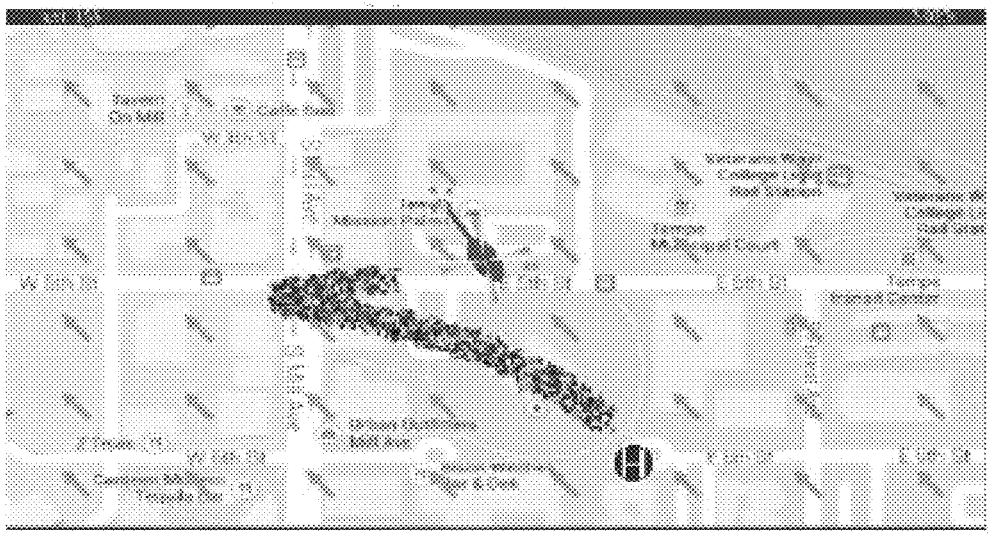

1) Tasks: Subjects completed tasks by controlling a virtual helicopter (FIGS. 4A and 4B) with the control paradigm described above. The goal of each task is to move a helicopter from the center of the screen along a defined path towards a helipad near an edge of the monitor. Paths were generated using bezier curves, and points were accumulated by collecting colored particles along the path within time constraints. After the allotted time passed at a given point on the path, the particles could no longer be collected for points. The trial was complete once the helicopter remains on the helipad for one second. After each trial, the map shifted the helicopter back to the center of the screen, and a new helipad and path appeared for the next trial following a five second break.

Throughout the experiment three different task variations were introduced (FIGS. 4A and 4B):

1) Control Tasks: No external forces applied throughout the task. The helicopter moves similar to velocity control.

2) Anisotropic Tasks: Constant external forces applied throughout the task, Subjects must use anisotropic stiffness to negate the effects of the external forces while moving along the path.

3) Isotropic Tasks: No external forces are generated until the helicopter reaches the helipad. Then forces are exerted in a random direction until the task is complete. Subjects must increase isotropic stiffness while landing to negate the effects of the external forces being exerted in an unknown direction.

External forces are applied with a magnitude proportional to 75% MVC, such that subjects must use different control strategies for anisotropic and isotropic tasks. With 75% MVC required to prevent external forces from displacing the helicopter, it would be difficult and exhausting for subjects to use isotropic stiffness to complete anisotropic tasks.

2) Sessions: The first session provided a ten minute exploration phase to help subjects learn basic movements and become familiar with the tasks. After ten minutes, subjects completed 50 control tasks.

Subjects returned on separate days for each of sessions two and three, completing an additional 50 control tasks without the initial exploration time. With only control tasks, subjects focused on learning directional movements with both speed and precision for the first 150 tasks.

Session four introduced external forces, and subjects were asked to complete 75 trials. The tasks were distributed as 50% control tasks, 25% anisotropic tasks, and 25% isotropic tasks.

TABLE I

EVALUATION METRICS

| Metric | Linear Learning Fit |
| --- | --- |
| Completion Time (CT) | $CT(n) = \kappa_{ct} - \beta_{ct} n$ |
| Throughput (TP) | $TP(n) = \kappa_{tp} + \beta_{tp} n$ |
| Task Score (TS) | $TS(n) = \kappa_{ts} + \beta_{ts} n$ |

Subjects were able to detect anisotropic tasks before the task started, but were unaware whether the other 75% of trials were control tasks or isotropic tasks until arriving at the helipad. This encouraged subjects to land with high isotropic stiffness in every trial. Session five provided the same task distribution for 75 additional trials, a total of 300 trials over the entire experiment.

3) Robot Demonstration: One subject returned after one month to demonstrate the control method on a robotic system. External forces were exerted via an elastic band as the subject completed various tasks grasping clothespins.

D. Data Analysis

Trials were analyzed based on performance metrics from all subjects. No quantifiable data was collected for the robot demonstration, as its intent is a proof of concept for intuitive transfer to physical systems.

1) Learning Trends: Metrics used for assessing performance throughout all five sessions are provided in Table I, using first degree polynomials to fit the results with respect to trial number for control tasks.

CT is the task completion time. TP is the throughput, a measure of speed and accuracy 1221. TS is the task score, a measure of speed and precision following the indicated path. n is the overall trial number, k is initial performance, and β shows the learning rate indicative of better performance over time.

Paths are randomly generated using cubic Bezier curves:

$$B(z) = (1-z)^3 P_o + 3(1-z)^2 P_1 + 3(1-z)^2 P_2 + z^3 P_3 \qquad (7)$$

where $P_o$ and $P_3$ are the origin and helipad position, respectively, and $P_{1,2}$ are random points on the screen. Particles are distributed at random offsets $$R + B(z), \forall R_i \in \left[-\frac{r}{2}, \frac{r}{2}\right],$$

through uniform samples of $t \in [0,1]$, with r the radius of the helicopter. Particles begin to disappear sequentially along the path three seconds after the start of the trial, until the last particle disappears eight seconds after the start of the trial. This encourages the subject to balance speed and precision while reaching the target, and TS is the number of particles collected over the total number of particles.

Task difficulty is given via the Shannon Formulation:

$$ID = \log_2\left(\frac{D}{W_D} + 1\right) \qquad (8)$$

where $W_D$ is the constant helipad diameter and $D = \int B(z) dt$ is the path distance. Then, $$TP = \frac{ID}{CT}.$$

2) External Force Impact: The specific impact of external forces is observed through changes in percentage of multiple muscle control PM. Although subjects could theoretically complete all tasks using only single muscle activations, optimal performance, both with and without external forces, requires a more direct path involving simultaneous activity from multiple muscles. PM measures the percentage of time that subjects activate two or more muscles for a given trial.

III. Results

Five healthy subjects (all male, age 20-28) participated in the experiment. All subjects gave informed consent as approved by the ASU IRB (Protocol: #1201007252). Subjects reported no fatigue throughout the first three sessions, but slight fatigue during sessions four and five due to the high muscle activity required to overcome external forces.

A. Learning Trends

Figure 5:
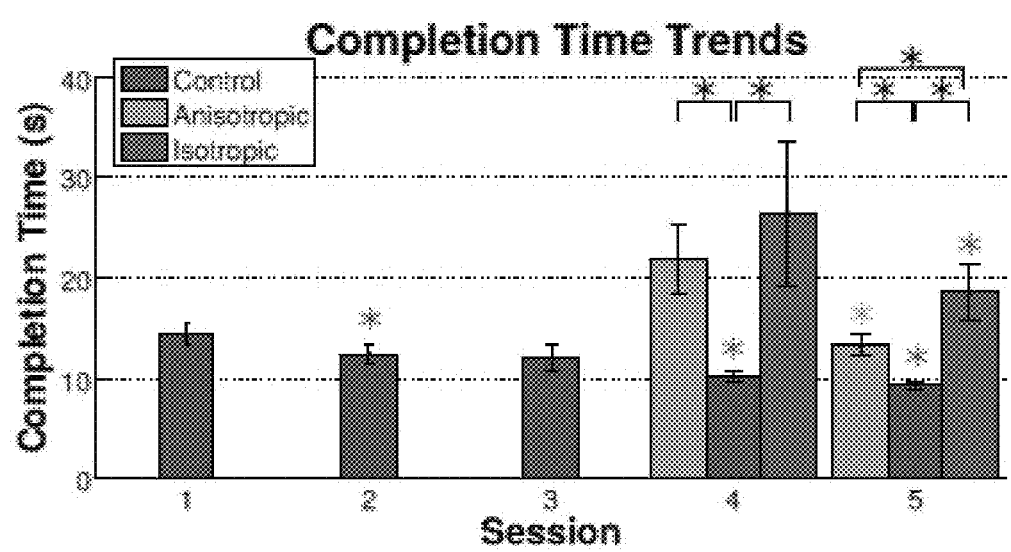
FIG. 5 is a graph showing VR completion times per trail across all subjects separated by task type.
Figure 6:
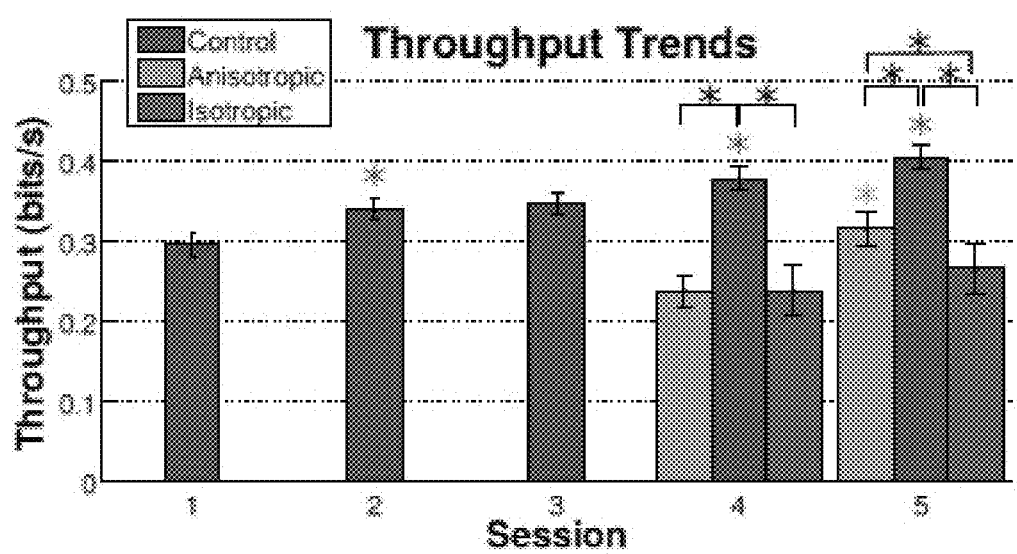
FIG. 6 is a graph showing VR throughput per trial across all subjects separated by task type.
Figure 7:
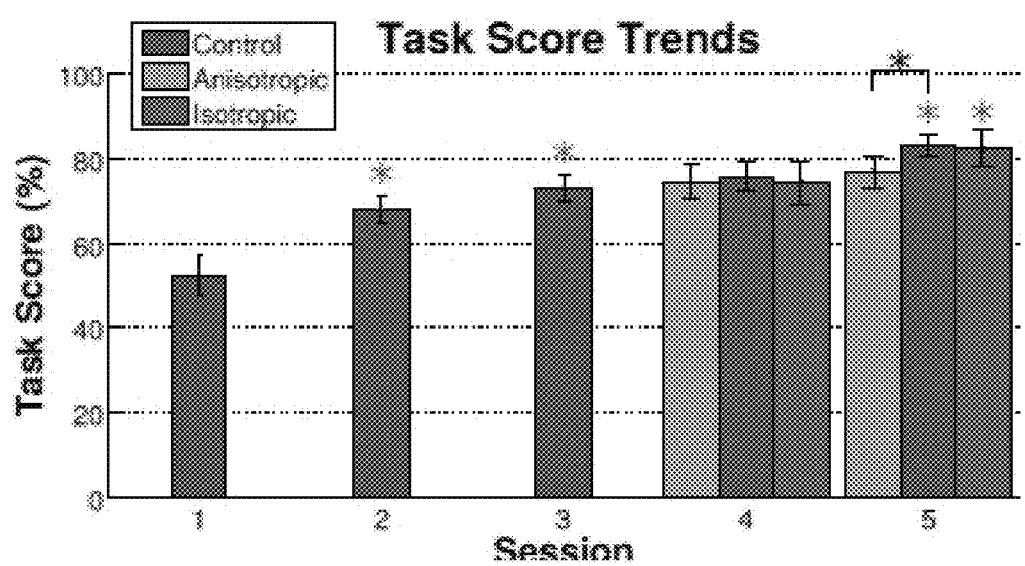
FIG. 7 is a graph showing VR scores per trial across all subjects separated by task type.

CT, TP and TS from all control trials were fit to Table I, with parameter values presented in Table II. Each metric shows a significant learning rate (β>0,p<0.05) despite time off between sessions. Performance metric progression for each task is shown in FIGS. 5, 6 and 7. The introduction of external forces significantly increased task difficulty, and accordingly reduced performance in session 4 compared to control tasks. However, the increased performance between session four and five show that subjects to control stiffness to stabilize control and improve performance over time, similarly to the control tasks throughout all five sessions. FIGS. 8A-8I are graphs that visualize the learning process for each task type with respect to the desired and actual paths taken by subjects.

B. External Force Impact

Figures 8A, 8B, 8C:
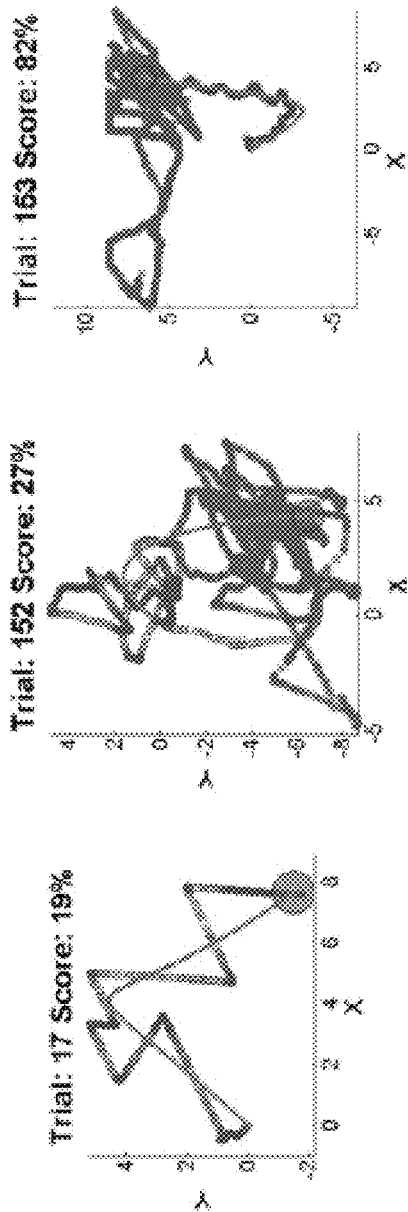
FIGS. 8A-8I are graphs showing scores for example tasks from VR with each column illustrating the control progression for each task type.
Figures 8D, 8E, 8F:
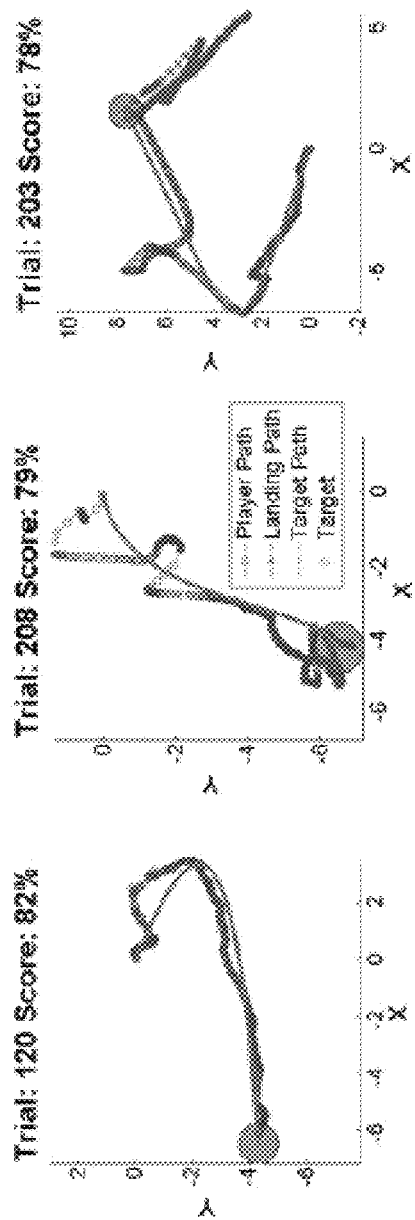
Figures 8G, 8H, 8I:
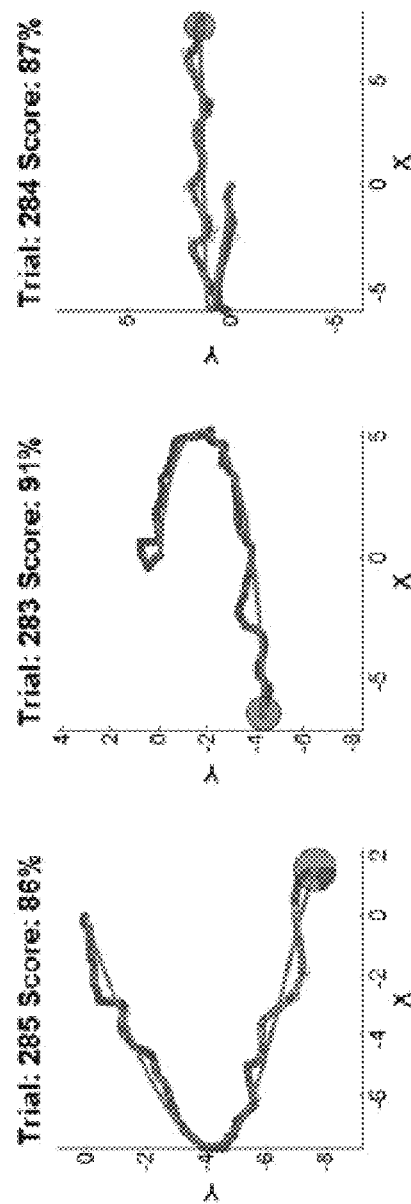
Figure 9:
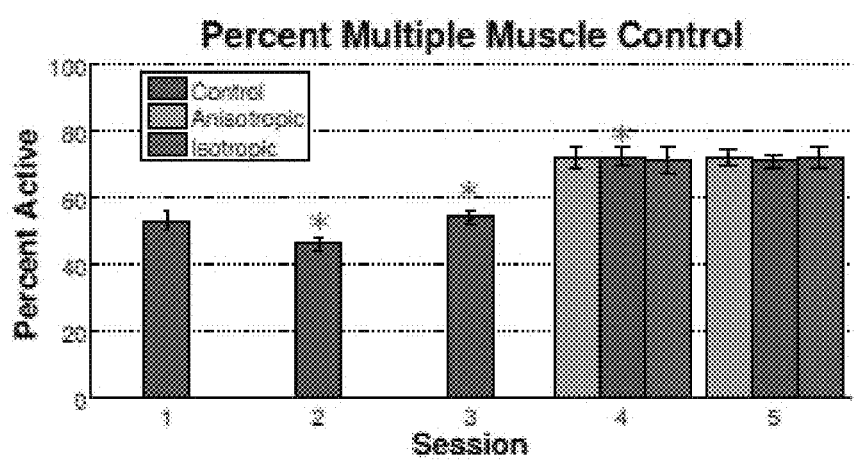
FIG. 9 is a graph showing the VR percent of simultaneous muscle activities during each trial.
Figure 10A:
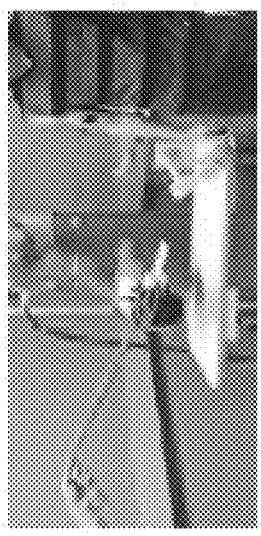
FIGS. 10A-10D are pictures showing example tasks from a robot demonstration with respect to anisotropic stiffness and isotropic stiffness.
Figure 10B:
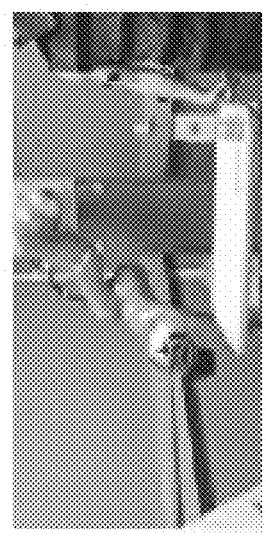
Figure 10C:
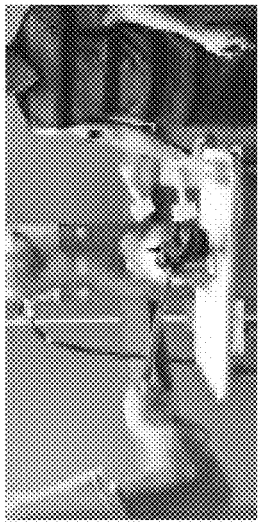
Figure 10D:

During control tasks, subjects can use single muscle contractions to coarsely follow the path (FIG. 8A). However, the optimal inputs involve multiple muscles to smoothly transition around curves. The introduction of external forces required simultaneous muscle activity to increase stiffness while traveling along the path. This coordination transferred to the control tasks, where subjects significantly increased the use of multiple muscle activations compared to the first three sessions (see FIG. 9). This correlates with significant performance improvements on control tasks in sessions four and five, suggesting that subjects obtained better control of the overall system while interacting with external forces.

C. Robot Control

One subject returned after one month to apply controls to the robot. The subject reported the controls easy to remember, and intuitive to transfer. Example anisotropic and isotropic stiffness tasks are shown in FIG. 10.

IV. Systems

Figure 11:
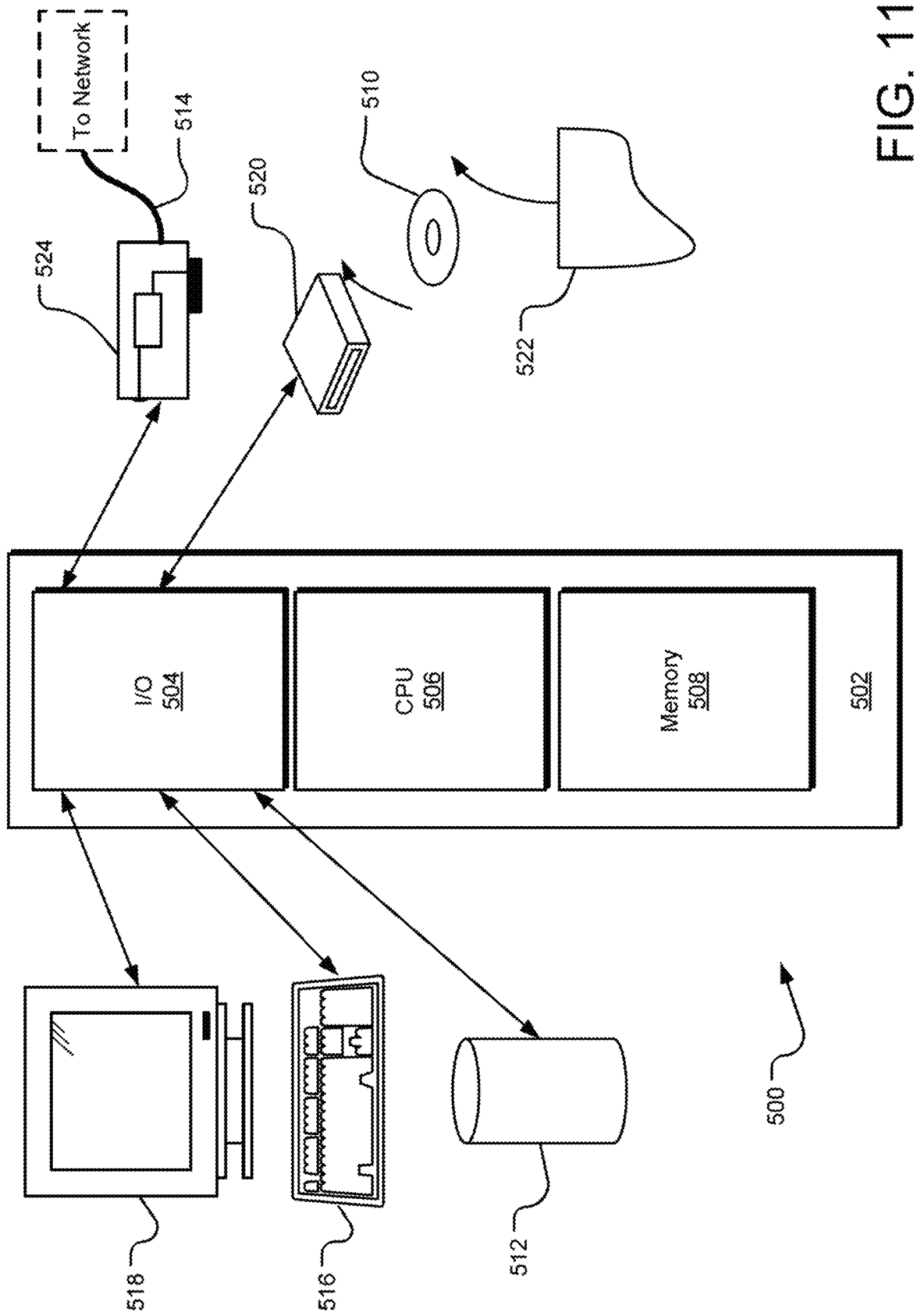
FIG. 11 illustrates an example computing system for implementing aspects of the presently disclosed technology.

Referring to FIG. 11, a detailed description of an example computing system 500 having one or more computing units that may implement various systems and methods discussed herein is provided. The computer system 500 may be a computing system is capable of executing a computer program product to execute a computer process. The computing system 500 may be applicable to the robot, the myoelectric interface, the VR interface, and/or other computing systems and computing systems. It will be appreciated that specific implementations of these devices may be of differing possible specific computing architectures not all of which are specifically discussed herein but will be understood by those of ordinary skill in the art.

The computer system 500 may be a general computing system is capable of executing a computer program product to execute a computer process. Data and program files may be input to the computer system 500, which reads the files and executes the programs therein. Some of the elements of a general purpose computer system 500 are shown in FIG. 11 wherein a processor 502 is shown having an input/output (I/O) section 504, a Central Processing Unit (CPU) 506, and a memory section 508. There may be one or more processors 502, such that the processor 502 of the computer system 500 comprises a single central-processing unit 506, or a plurality of processing units, commonly referred to as a parallel processing environment. The computer system 500 may be a conventional computer, a distributed computer, or any other type of computer, such as one or more external computers made available via a cloud computing architecture. The presently described technology is optionally implemented in software devices loaded in memory 508, stored on a configured DVD/CD-ROM 510 or storage unit 512, and/or communicated via a wired or wireless network link 514, thereby transforming the computer system 500 in FIG. 11 to a special purpose machine for implementing the described operations.

The I/O section 504 is connected to one or more user-interface devices (e.g., a keyboard 516 and a display unit 518), a disc storage unit 512, and a disc drive unit 520. In the case of a tablet device, the input may be through a touch screen, voice commands, and/or Bluetooth connected keyboard, among other input mechanisms. Generally, the disc drive unit 520 is a DVD/CD-ROM drive unit capable of reading the DVD/CD-ROM medium 510, which typically contains programs and data 522. Computer program products containing mechanisms to effectuate the systems and methods in accordance with the presently described technology may reside in the memory section 504, on a disc storage unit 512, on the DVD/CD-ROM medium 510 of the computer system 500, or on external storage devices made available via a cloud computing architecture with such computer program products, including one or more database management products, web server products, application server products, and/or other additional software components. Alternatively, a disc drive unit 520 may be replaced or supplemented by an optical drive unit, a flash drive unit, magnetic drive unit, or other storage medium drive unit. Similarly, the disc drive unit 520 may be replaced or supplemented with random access memory (RAM), magnetic memory, optical memory, and/or various other possible forms of semiconductor based memories commonly found in smart phones and tablets.

The network adapter 524 is capable of connecting the computer system 500 to a network via the network link 514, through which the computer system can receive instructions and data. Examples of such systems include personal computers, Intel or PowerPC-based computing systems, AMD-based computing systems and other systems running a Windows-based, a UNIX-based, or other operating system. It should be understood that computing systems may also embody devices such as terminals, workstations, mobile phones, tablets, laptops, personal computers, multimedia consoles, gaming consoles, set top boxes, and the like.

When used in a LAN-networking environment, the computer system 500 is connected (by wired connection or wirelessly) to a local network through the network interface or adapter 524, which is one type of communications device. When used in a WAN-networking environment, the computer system 500 typically includes a modem, a network adapter, or any other type of communications device for establishing communications over the wide area network. In a networked environment, program modules depicted relative to the computer system 500 or portions thereof, may be stored in a remote memory storage device. It is appreciated that the network connections shown are examples of communications devices for and other means of establishing a communications link between the computers may be used.

In an example implementation, robot interfaces, VR interfaces, myoelectric interfaces, multidirectional impedance control software and other modules and services may be embodied by instructions stored on such storage systems and executed by the processor 502. Some or all of the operations described herein may be performed by the processor 502. Further, local computing systems, remote data sources and/or services, and other associated logic represent firmware, hardware, and/or software configured to control operations of the robot, the various interfaces, the electrodes, and/or other computing units or components of the systems and devices described herein. Such services may be implemented using a general purpose computer and specialized software (such as a server executing service software), a special purpose computing system and specialized software (such as a mobile device or network appliance executing service software), or other computing configurations. In addition, one or more functionalities of the systems and methods disclosed herein may be generated by the processor 502 and a user may interact with a Graphical User Interface (GUI) using one or more user-interface devices (e.g., the keyboard 516, the display unit 518, and other user devices) with some of the data in use directly coming from online sources and data stores.

The system set forth in FIG. 11 is but one possible example of a computer system that may employ or be configured in accordance with aspects of the present disclosure. It will be appreciated that other non-transitory tangible computer-readable storage media storing computer-executable instructions for implementing the presently disclosed technology on a computing system may be utilized.

In the present disclosure, the methods disclosed may be implemented as sets of instructions or software readable by a device. Further, it is understood that the specific order or hierarchy of steps in the methods disclosed are instances of example approaches. Based upon design preferences, it is understood that the specific order or hierarchy of steps in the method can be rearranged while remaining within the disclosed subject matter. The accompanying method claims present elements of the various steps in a sample order, and are not necessarily meant to be limited to the specific order or hierarchy presented.

The described disclosure may be provided as a computer program product, or software, that may include a non-transitory machine-readable medium having stored thereon instructions, which may be used to program a computer system (or other electronic devices) to perform a process according to the present disclosure. A machine-readable medium includes any mechanism for storing information in a form (e.g., software, processing application) readable by a machine (e.g., a computer). The machine-readable medium may include, but is not limited to, magnetic storage medium; optical storage medium; magneto-optical storage medium; read only memory (ROM); random access memory (RAM); erasable programmable memory (e.g., EPROM and EEPROM); flash memory; or other types of medium suitable for storing electronic instructions.

The description above includes example systems, methods, techniques, instruction sequences, and/or computer program products that embody techniques of the present disclosure. However, it is understood that the described disclosure may be practiced without these specific details.

It should be understood from the foregoing that, while particular implementations have been illustrated and described, various modifications can be made thereto without departing from the spirit and scope of the invention as will be apparent to those skilled in the art. Such changes and modifications are within the scope and teachings of this invention as defined in the claims appended hereto.

What is claimed is:

1. A method for controlling a robot, the method comprising:
   receiving a set of one or more surface electromyography inputs for one or more muscles at one or more computing units in communication with a myoelectric interface for the robot;
   mapping the set of one or more surface electromyography inputs to a set of one or more control outputs for a motion of the robot;
   generating one or more stiffness outputs for the motion of the robot based on the set of one or more surface electromyography inputs, the one or more stiffness outputs each assigned a stiffness direction to a same axis as a corresponding muscle motion; and
   providing a multidirectional impedance control of the robot with one or more degrees of freedom via the myoelectric interface, the multidirectional impedance control based on the one or more stiffness outputs and the set of one or more control outputs, the multidirectional impedance control having a primary stiffness decoupled from a primary motion.

2. The method of claim 1, wherein the robot is a prosthetic upper or lower limb.

3. The method of claim 1, wherein a direction of the primary stiffness is different from a direction of the primary motion.

4. The method of claim 1, wherein the primary stiffness is achieved without the primary motion.

5. The method of claim 1, wherein a magnitude of the set of one or more control outputs is independent of a magnitude of the set of one or more surface electromyography inputs.

6. The method of claim 1, wherein a magnitude of the one or more stiffness outputs is proportional to a magnitude of the set of one or more surface electromyography inputs.

7. The method of claim 1, wherein mapping the set of one or more surface electromyography inputs to the set of one or more control outputs involves collecting, rectifying, filtering, and normalizing the set of one or more surface electromyography inputs with respect to a maximal voluntary contraction for each of the one or more muscles.

8. The method of claim 7, wherein the set of one or more surface electromyography inputs are filtered with a low-pass filter.

9. The method of claim 1, wherein the set of one or more surface electromyography inputs are scaled based on a maximal voluntary contraction for each of the one or more muscles.

10. The method of claim 1, wherein the motion of the robot involves at a control task, an isotropic task, or an anisotropic task.

11. The method of claim 1, wherein the multidirectional impedance control is further based on an application of an external force.

12. The method of claim 1, wherein the multidirectional impedance control is further based on an isotropic damping term.

13. One or more non-transitory tangible computer-readable storage media storing computer-executable instructions for performing a computer process on a computing system, the computer process comprising:
    receiving a set of one or more surface electromyography inputs for one or more muscles;
    mapping the set of one or more surface electromyography inputs to a set of one or more control outputs for a motion of the robot;
    generating one or more stiffness outputs for the motion of the robot based on the set of one or more surface electromyography inputs, the one or more stiffness outputs each assigned a stiffness direction to a same axis as a corresponding muscle motion; and
    providing a multidirectional impedance control of the robot with one or more degrees of freedom based on the one or more stiffness outputs and the set of one or more control outputs, the multidirectional impedance control having a primary stiffness decoupled from a primary motion.

14. The one or more non-transitory tangible computer-readable storage media of claim 13, wherein a direction of the primary stiffness is different from a direction of the primary motion.

15. The one or more non-transitory tangible computer-readable storage media of claim 13, wherein the primary stiffness is achieved without the primary motion.

16. The one or more non-transitory tangible computer-readable storage media of claim 13, wherein a magnitude of the set of one or more control outputs is independent of a magnitude of the set of one or more surface electromyography inputs.

17. The one or more non-transitory tangible computer-readable storage media of claim 13, wherein a magnitude of the one or more stiffness outputs is proportional to a magnitude of the set of one or more surface electromyography inputs.

18. The one or more non-transitory tangible computer-readable storage media of claim 13, wherein mapping the set of one or more surface electromyography inputs to the set of one or more control outputs involves collecting, rectifying, filtering, and normalizing the set of one or more surface electromyography inputs with respect to a maximal voluntary contraction for each of the one or more muscles.

19. A system for controlling a robot, the system comprising:
- one or more surface electromyography electrodes configured to capture a set of one or more surface electromyography inputs for one or more muscles;
- one or more computing units in communication the one or more surface electromyography electrodes, the one or more computing units mapping the set of one or more surface electromyography inputs to a set of one or more control outputs for a motion of the robot and generating one or more stiffness outputs for the motion of the robot based on the set of one or more surface electromyography inputs, the one or more stiffness outputs each assigned a stiffness direction to a same axis as a corresponding muscle motion; and
- a myoelectric interface in communication with the one or more computing units, the one or more computing units providing a multidirectional impedance control of the robot via the myoelectric interface with one or more degrees of freedom based on the one or more stiffness outputs and the set of one or more control outputs, the multidirectional impedance control having a primary stiffness decoupled from a primary motion.

20. The system of claim 19, wherein the myoelectric interface is in communication with the one or more computing units via at least one of a wired or wireless connection.

* * * * *